US005108899A

United States Patent [19]

Allen

[11] Patent Number: 5,108,899

[45] Date of Patent: Apr. 28, 1992

[54] CHEMILUMINESCENCE ASSAY OF IN VIVO INFLAMMATION

[75] Inventor: Robert C. Allen, Little Rock, Ark.

[73] Assignee: EXOxEmis, Inc., San Antonio, Tex.

[21] Appl. No.: 429,105

[22] Filed: Oct. 31, 1989

[51] Int. Cl.$^5$ .................... G01N 33/567; G01N 33/48

[52] U.S. Cl. .................................. 435/7.21; 435/968; 435/975; 436/63; 436/503

[58] Field of Search ...................... 435/7.21, 7.2, 7.24, 435/29, 25, 34, 39, 968; 436/63, 172, 503, 519, 821

[56] References Cited

U.S. PATENT DOCUMENTS

| | | | |
|---|---|---|---|
| 3,689,391 | 9/1972 | Ullman | 204/159 |
| 3,996,345 | 12/1976 | Ullman et al. | 424/12 |
| 3,998,943 | 12/1976 | Ullman | 424/12 |
| 4,104,029 | 8/1978 | Maier, Jr. | 23/230 B |
| 4,160,645 | 7/1979 | Ullman | 23/230 B |
| 4,161,515 | 7/1979 | Ullman | 424/8 |
| 4,220,450 | 9/1980 | Maggio | 424/12 |
| 4,231,754 | 11/1980 | Vogelhut | 23/230 R |
| 4,238,195 | 12/1980 | Boguslaski et al. | 23/230 B |
| 4,256,834 | 3/1981 | Zuk et al. | 435/7.72 |
| 4,269,938 | 5/1981 | Frank | 435/7.9 |
| 4,277,437 | 7/1981 | Maggio | 422/61 |
| 4,302,534 | 11/1981 | Halmann et al. | 435/6 |
| 4,372,745 | 2/1983 | Mandle et al. | 436/537 |
| 4,380,580 | 4/1983 | Boguslaski et al. | 435/5 |
| 4,383,031 | 5/1983 | Boguslaski et al. | 435/7.72 |
| 4,436,715 | 3/1984 | Schaap et al. | 423/579 |
| 4,478,817 | 10/1984 | Campbell et al. | 424/7.1 |
| 4,521,511 | 6/1985 | Stout | 435/28 |
| 4,598,044 | 7/1986 | Kricka et al. | 435/28 |
| 4,729,950 | 3/1988 | Kricka et al. | 435/28 |

FOREIGN PATENT DOCUMENTS 235970 9/1987 European Pat. Off. .

OTHER PUBLICATIONS

Van Dyke et al., Meth. Enzymology 133:493-507, 1986.

Fearon et al., J. Immunol. 130(1):370-375, 1983.

(List continued on next page.)

*Primary Examiner*—Esther L. Kepplinger
*Assistant Examiner*—Donna C. Wortman
*Attorney, Agent, or Firm*—Christensen, O'Connor, Johnson & Kindness

[57] ABSTRACT

The presence or amount of in vivo inflammation of a patient is determined by comparing the extent of opsonin receptor expression in vivo on phagocytes of a patient with the maximum opsonin receptor expression inducible on phagocytes of the patient in vitro after stimulation with a receptor expression priming agent. Preferably, the in vivo state of inflammation of a patient is determined by contacting a first portion of a phagocyte containing biological sample from the patient with a opsonified oxidative metabolism stimulating agent capable of eliciting metabolic activation and with a chemiluminigenic substrate, contacting a second portion of the biological sample from the patient with an opsonin receptor expression priming agent, an opsonfield oxidative metabolism stimulating agent capable of eliciting metabolic activation and a chemiluminigenic substrate, and then comparing the chemiluminescence response of the first and second portions of the sample as a measure of the immune response potential or state of inflammation of the patient. Phagocyte function is additionally quantitatively evaluated by measuring the phagocyte oxygenation capacity of a maximally opsonin receptor primed and stimulated biological sample of a patient, determining the specific oxygenation capacity per phagocyte in the sample, and comparing the specific oxygenation capacity to a set of controls representing the normal distribution of specific oxygenation established from testing a large population. The phagocyte-specific oxygenation capacity is determined by contacting the sample with an opsonin receptor expression priming agent, an opsonified oxidative metabolism stimulating agent and a chemiluminigenic substrate, measuring the chemiluminescence response of the sample, determining the chemiluminescence response per phagocyte of the sample and comparing the response per phagocyte with that of the normal range of values. Kits and reagents are provided for use in the practice of the disclosed methods.

60 Claims, 6 Drawing Sheets

OTHER PUBLICATIONS

Allen, Meth. Enzymology 133:449–493, 1986.

Seitz, W. R., "Chemiluminescence Detection of Enzymically Generated Peroxide", *Methods in Enzymology,* LVII, 445–462, 1978.

Klebanoff, "Myeloperoxidase–Halide–Hydrogen Peroxide Antibacterial System," *J. Bacteriol.,* 95, 2131–2138, 1968.

Allen, R. C., Dissertation entitled "Studies on the Generation of Electronic Excitation States in Human Polymorphonuclear Leukocytes and their Participation in Microbicidal Activity", Jul., 1973.

Allen, R. C. et al., "Evidence for the Generation of an Electronic Excitation State(s) in Human Polymorphonuclear Leukocytes and its Participation in Bactericidal Activity", *Biochemical and Biophysical Research Communications,* 47(4), 679–684, 1972.

Allen, R. C., "Halide Dependence of the Myeloperoxidase–Mediated Antimicrobial System of the Polymorphonuclear Leukocyte in the Phenomenon of Electric Excitation", *Biochemical and Biophysical Research Communications,* 63(3), 675–683, 1975.

Allen, R. C., "The Role of pH in the Chemiluminescent Response of the Myeloperoxidase–Halide–HOOH Antimicrobial System", *Biochemical and Biophysical Research Communications,* 63(3), 684–691, 1975.

Allen, R. C. and L. D. Loose, "Phagocytic Activation of a Luminol–Dependent Chemiluminescence in Rabbit Alveolar and Peritoneal Macrophages", *Biochemical and Biophysical Research Communications,* 69(1), 245–252, 1976.

Allen, R. C., "Evaluation of Serun Opsonic Capacity by Quantitating the Initial Chemiluninescent Response from Phagocytizing Polymorphonuclear Leukocytes", *Infection and Immunity,* 15(3), 828–833, 1977.

Allen, R. C. et al., "Correlation of Metabolic and Chemiluminescent Responses of Granulocytes from Three Female Siblings with Chronic Granulomatous Disease", *Journal of Infectious Diseases,* 136(4), 510–518, 1977.

Allen, R. C., "Reduced Radical, and Excited State Oxygen in Leukocyte Microbicidal Activity", In J. T. Dingle, P. J. Jacques and J. H. Shaw [eds.] Lysosomes in Applied Biology and Therapeutics, North–Holland Publishing Company, 1979, pp. 197–233.

Allen, R. C., "Chemiluminescence: An Approach to the Study of the Humoral–Phagocyte Axis in Host Defense Against Infection", In Liquid Scintillation Counting, Recent Applications and Development, vol. II. Sample Preparation and Applications, Academic Press, Inc., 1980, pp. 377–393.

Allen, R. C. et al., "Role of Myeloperoxidase and Bacterial Metabolism in Chemiluminescence of Granulocytes from Patients with Chronic Granulomatous Disease", *Journal of Infectious Disease,* 144(4), 344–348, 1981.

Allen, R. C. et al., "Humoral–Phagocyte Axis of Immune Defense in Burn Patients", *Archives of Surgery,* 117, 133–140, 1982.

Allen, R. C., "Direct Quantification of Phagocyte Activity in Whole Blood: A Chemiluminigenic Probe Approach", In E. Kaiser, F. Gabl, M. M. Muller and P. M. Bayer [eds.] Proceedings of XI International Congress of Clinical Chemistry, Vienna, 1981. Walter de Gruyter, Berlin, New York, 1982, pp. 1043–1058.

Allen, R. C., "Biochemiexcitation: Chemiluminescence and the Study of Biological Oxygenation Reactions", In W. Adam and G. Cilento [eds.] Chemical and Biological Generation of Excited States, Acadamic Press, Inc., New York, 1982, pp. 309–344.

Allen, R. C., "Chemiluminescence and the Study of Phagocyte Redox Metabolism", In F. Rossi and P. Patrisica [eds.] Biochemistry and Function of Phagocytes, Plenum Publishing Corporation, 1982, pp. 411–421.

Allen, R. C. and M. M. Lieberman, "Kinetic Analysis of Microbe Opsonification Based on Stimulated Polymorphonuclear Leukocyte Oxygenation Activity", *Infection and Immunity* 45(2), 475–482, 1984.

Allen, R. C. "Phagocytic Leukocyte Oxygenation Activities and Chemiluminescence: A Kinetic Approach to Analysis", In Marlene A. DeLuca and William D. McElroy [eds.] Methods in Enzymology, vol. 133, Bioluminescence and Chemiluminescence, Academic PRess, Inc., 1986, pp. 449–493.

Allen, R. C., "Oxygen–Dependent Microbe Killing by Phagocyte Leukocytes: Spin Conservation and Reaction Rate", In W. Ando and Y. Moro–oka [eds.] The Role of Oxygen in Chemistry and Biochemistry, Proceedings of an International Symposium on Activation of Dioxygen and Homogeneous Catalytic Oxidations, Tsukuba, Japan, 12–16 Jul. 1987, *Studies in Organic*

*Chemistry,* vol. 33, pp. 425–434, 1988 Elsevier Science Publishers B. V. Amsterdam.
Steinbeck, M. J. and J. A. Roth, "Neutrophil Activation by Recombinant Cytokines", *Reviews of Infectious Diseases,* 11(4), 549–568, 1989.
Malech, H. L. and J. I. Gallin, "Medical Intelligence, Neutrophils in Human Diseases", *New England Journal of Medicine,* 317(11), 687–694, 1987.
Olsson, I. and P. Venge, "The Role of the Human Neutrophil in the Inflammatory Reaction", *Allergy,* 35, 1–13, 1980.
Cooper, N. R., "Assays for Complement Activation", In Robert M. Nakamura and David T. Rowlands [eds.] Clinics in Laboratory Medicine, Advances in Immunopathology, vol. 6, No. 1, pp. 139–155, Mar. 1986, W. B. Saunders Co.
Chenoweth, D. E., "Complement Mediators of Inflammation", In Gordon D. Ross [ed.] Immunobiology of the Complement System, An Introduction for Research and Clinical Medicine, pp. 63–86, Academic Press, 1986.
Fearon, D. T. and L. A. Collins, "Increased Expression of C3b Receptors on Polymorphonuclear Leukocytes Induced by Chemotactic Factors and by Purification Procedures", *J. Immunology* 130(1), 370–175, 1983.
Fearon, D. T. and W. W. Wong, "Complement Ligand-Receptor Interactions that Mediate Biological Responses", *Ann. Rev. Immunol.* 1, 243–271, 1983.
Dure, L. S. and J. J. Cormier, "Studies on the Bioluminescence of *Balanoglossus biminiensis* Extracts, III. A Kinetic Comparison", *Journal of Biological Chemistry,* 239(7), 1964.
Kopecky, K. R., "Synthesis of 1,2–Dioxetanes", In Waldemar Adam and Giuseppe Cilento [eds.] Chemical and Biological Generation of Excited States, Academic Press, 1982, pp. 85–114.
Bronstein, I. et al., "1,2–Dioxetanes: Novel Chemiluminescent Enzyne Substrates. Applications to Immunoassays", *Journal of Bioluminescence and Chemiluminescence,* 4, 99–111, 1989.
McCara, F. et al., "Luminescent Labels for Immunossay—From Concept to Practice", *Journal of Bioluminescence and Chemiluminescence,* 4, 51–18, 1989.
Kearns, D. R. and A. U. Khan, "Sensitized Photooxygenation Reactions and the Role of Singlet Oxygen", *Photochemistry and Photobiology,* 10, 193–210, 1969.
Kanofsky, J. R., "Singlet Oxygen Production by Lactoperoxidase", *Journal of Biological Chemistry,* 258(10), 5991–5993, 1983.

LUMINESCENCE ASSAY OF *in vivo* INFLAMMATION

| *in vivo* | | *in vitro* | |
|---|---|---|---|
| PHAGOCYTE-HUMORAL INTERACTION | CIRCULATING PHAGOCYTE | BLOOD OR OTHER SAMPLE DILUTED AND ADDED TO CHEMILUMINIGENIC-SUBSTRATE COMPLETE MEDIUM (CLS-CM), PLUS COMPLEMENT- AND/OR IgG-OPSONIFIED STIMULUS, ($S_{opsn}$). | THE SAME SAMPLE DILUTED AND ADDED TO CLS-CM, PLUS OPTIMUM ADDITIONAL PRIMER STIMULUS (eg: C5a, NfMLP, etc) TO MAXIMIZE EXPRESSION OF OPSONIN RECEPTORS (eg: CR3, FcR, etc), ($S_{prim}^{max}$), PLUS COMPLEMENT- AND/OR IgG-OPSONIFIED STIMULUS, ($S_{opsn}$). |
| PHAGOCYTE IN INITIAL, UNSTIMULATED STATE, ($P_{init}$). INFLAMMATORY STATE GENERATED PRIMER STIMULI, ($S_{prim}$). eg. C5a | INFLAMATION AFFECTS THE OPSONIN RECEPTOR EXPRESSION OF THE CIRCULATING PHAGOCYTE, ($P_{circ}$). | | |
| $[P_{init}][S_{prim}]a=[P_{circ}] \Longrightarrow$ | | $[P_{circ}][S_{opsn}]c=[P^*]$<br>$[P^*][CLS]e=CL$ | $[P_{circ}][S_{prim}^{max}]b=[P_{max}]$<br>$[P_{max}][S_{opsn}]d=[P^*_{max}]$<br>$[P^*_{max}][CLS]f=CL_{max}$ |

*In vivo* INFLAMMATORY STATE ASSESSED *in vitro* AS THE CL KINETIC RATIO:

$$\frac{CL}{CL_{max}} = \frac{\text{RECEPTOR EXPRESSION in vivo} \rightarrow \text{ACTIVATION KINETICS} \rightarrow CL}{\text{MAXIMUM RECEPTOR EXPRESSION} \rightarrow \text{ACTIVATION KINETICS} \rightarrow CL}$$

FIG. 1.

CHEMILUMINESCENCE ASSAY OF IN VIVO INFLAMMATION

FIELD OF THE INVENTION

The present invention relates to methods for evaluating the in vivo state of inflammation of a patient. More particularly, the present invention relates to chemiluminescence methods for monitoring phagocyte response potential of a patient as an indication of immune system condition.

BACKGROUND OF THE INVENTION

Inflammation is the reaction of an organism to injury and an initiator of the healing process. Local symptoms of inflammation include heat (calor), redness (rubor), swelling (tumor) and pain (dolor), and may be readily apparent on physical examination of a patient. Acute inflammation, the primary mechanism of host immune protection against infectious or harmful agents, is the consequence of complex ligand-receptor interactions involving the humoral and phagocyte components of immunity. Systemic inflammation is not as easy to identify and/or quantify as local inflammation. Fever and leukocytosis (i.e., transient increase in the number of leukocytes in the blood) are the most prominent systemic manifestations of acute inflammation. The leukocytosis is a neutrophilia (i.e., increase in the number of polymorphonuclear neutrophil leukocytes or PMNLs) in most bacterial infections, and an eosinophilia (i.e., increase in the number of eosinophils) in most allergic diseases and parasitic infestations. Many viral diseases are associated with relative or absolute lymphocytosis (i.e., increase in the number of lymphocytes), whereas certain viral, richettsial, bacterial, and protozoan infections are characterized by leukopenia (i.e., a reduction in the number of leukocytes). The intensity of the inflammatory response is related to the severity of injury and the humoral/immune system reaction capacity of the host.

The immunoglobulin dependent and independent activation of the classical and alternative pathways, respectively, of complement provide the principle humoral effector mechanisms of inflammation. Activation of either pathway results in a cascade of proteolytic activities generating anaphylatoxins, i.e., freely diffusible ligands such as the relatively low molecular weight complement fragments, C5a and C3a. This activity also generates opsonin. The larger molecular weight complement fragment C3b is an opsonin that covalently reacts with and fixes to a broad variety of molecules present on microbial surfaces, and prepares the surfaces for attack by phagocytes (a process referred to as opsonification).

Although endothelial cells, platelets, eosinophils, basophils and lymphocytes play specialized roles, the polymorphonuclear neutrophil leukocyte (PMNL) and monocyte are the principle cellular effectors of the acute inflammatory response. The humoral-phagocyte relationship can be conceptualized as an information-effector mechanism for rapid response to infection or injury. The complement system responds to general classes of foreign substances, e.g., certain polysaccharides, as well as specific antigens via antigen-specific immunoglobulins. The location and magnitude of the infection or injury is transmitted to the various cellular effectors of inflammation via an enzymatically amplified cascade of protolytic activity. The smaller molecular weight anaphylatoxins produced (e.g., C5a, as well as certain bacterial peptide markers of bacterial infection, such as N-formyl methionyl peptides (e.g., N-fMLP), diffuse from the site of generation inducing the localized tissue changes characteristic of inflammation and serving to establish a chemotactic concentration gradient. The opsonic products of activation (e.g., C3b) bind to the initiator substance, e.g., a microbe. As a result, local hemodynamic changes and endothelial alterations promote phagocyte margination, sticking, diapedesis, and migration to the site of inflammation where contact with the complement and/or immunoglobulin opsonified foreign substance, results in 1) phagocyte recognition of the opsonified material as a foreign substance via opsonin-specific receptors, 2) engulfment i.e., phagocytosis, and 3) the activation of microbicidal metabolism.

Microbicidal metabolism is characterized by non-mitochondrial $O_2$ consumption and glucose dehydrogenation via the hexose monophosphate shunt (Sbarra and Karnovsky, 1960, *J. Biol. Chem.* 234:1355). These activities reflect the activation of NAD(P)H oxidase (Rossi et al., *J. Reticuloendothel. Soc.* 12:127) yielding reduced oxygen products that can participate in microbicidal reactions (Review: Badwey and Karnovsky, 1980, *Annu. Rev. Biochem.* 49:695). Chemiluminescence, i.e., photon emission, is an energy product of these oxygenation reactions (Allen, 1972, *Biochem. Biophys. Res. Commun.* 47:679). The chemiluminescence quantum yield, i.e., the ratio of photons emitted per oxygenation event, is dependent on the type and quantity of generated oxygenating agents and the nature of the substrate oxygenated. The native luminescence product of phagocyte microbicidal action reflects the oxygenation of natural substrates presented. Such reactions are of relatively low quantum yield and vary with the nature of the substrate oxygenated. Introduction of exogenous high quantum yield chemiluminigenic substrates (CLS) overcomes the problems of variability and sensitivity. Luminol and other cyclic hydrazides increase quantum yield by greater than three orders of magnitude and at the same time impose control with regard to the substrate oxygenation measured (Allen and Loose, 1976, *Biochem. Biophys. Res. Commun.* 69:245). Acridinium compounds such as lucigenin can also be employed as CLS (Allen, 1981, in *Bioluminescence and Chemiluminescence: Basic Chemistry and Analytical Applications*, DeLuca and McElroy, eds., pp. 63–73, Academic Press, New York). However, these CLSs differ with regard to the type of oxygenation activity measured (Allen, 1982, in *Chemical and Biological Generation of Excited States*, Adam and Cilento, eds., pp. 309–344, Academic Press, New York, and Allen, 1986, in *Meth. Enzymol.* 133:449).

Complement activation plays the principle role in precipitating the acute inflammatory response. The complement system is composed of 20 different proteins that account for approximately 15% of the plasma globulins. In the past, measurement of the various complement proteins, products of activation, and functional capacity have provided the major avenues of approach to estimating the state of systemic inflammation (See: Cooper, 1986, in *Clinics in Laboratory Medicine: Advances in Immunopathology*, Volume 6, Number 1, Nakamura and Rowlands, eds., pp. 139–155, W. B. Saunders Comp., Philadelphia). Until recently, virtually all complement system testing was based on: 1) measuring the collective functionality of the system, e.g., $CH_{50}$ hemolytic assay, or 2) quantification of complement components, e.g., C3, C4, factor B. These techniques are limited in that they only measure the static plasma levels of specific complement system components, and not the dynamics of complement activation. Since synthesis is quite responsive to consumption and several components behave as acute phase reactants, these measurements are less than ideal for evaluating the state of inflammation of a patient.

More recently, several methodologies have been directed to detecting and quantifying the complement activation process. These activation-specific complement assays detect physical, chemical, or antigenic changes in complement components consequent to in vivo activation. The three general assay approaches used are based on detecting: 1) proteolytic alteration of a complement component, 2) alteration in antigenicity, or 3) protein-protein complexes that form as a result of complement activation.

Assays based on detecting proteolytic alteration of a complement component include the determination of C4d/C4 and C3d/C3 ratios. In a typical assay of this type, proteolytic product, e.g., C4d, is isolated from the residual parent component, e.g., C4, by electrophoresis, and both parent and product molecules are determined immunochemically, e.g., by rocket immunoelectrophoresis (See Curd, 1982, in *Analysis and Recent Progress in Diagnostic Laboratory Immunology*, Nakamura et al., eds., pp. 215–230, Masson Publ., Nurnberger and Bhadki, 1984, *J. Immunol. Meth.* 74:87). This approach is technically involved, time consuming, and relatively insensitive.

Radioimmunoassay of the anaphylatoxins C3a, C4a, and C5a provides a more sensitive methodology belonging to this first category (See Gorski, 1981, *J. Immunol. Meth.* 47:61; Hugli and Chenoweth, 1980, in *Future Perspectives in Clinical Laboratory Immunoassays*, Nakamura et al., eds., pp. 443–460, Alan R. Liss, Inc., New York). However, this approach is also technically involved, time consuming, and requires the use of radioisotopes.

An example in the second category of activation-specific assays (i.e., where an alteration in antigenicity is determined) is the disappearance of C1r but retention of C1s antigen expression following complement activation. This differential loss results from C1-inhibitor (C1In) binding. As such, the ratio of simultaneously determined C1r:C1s provides an expression of C1 activation (Ziccardi and Cooper, 1978, *J. Exp. Med.* 147:385) as well as C1In functional capacity of plasma (Ziccardi and Cooper, 1980, *Clin. Immunol. Immunopathol.* 15:465).

The third category of activation-specific assays relates to the determination of protein-protein complexes that form as a result of complement activation. Protein-protein complexes are characteristic of both classical, e.g., C1r-C1s-C1In, and alternative, e.g., Bb-C3bn-P, activation pathways. For example, in the Bb-C3bn-P complex enzyme-linked immunosorbent assay (ELISA) for detection of alternative pathway activation, a sample is contacted with surface-bound antiprotein P antibody which binds the complex as well as free protein P. After washing, the bound material is further contacted with anti-C3 antibody enzyme conjugate indicator system. Following washing and incubation with a substrate for color development, the degree of color development is related to the quantity of C3bn-P complex in the sample (Cooper et al., 1983, *Springer Sem. Immunopathol.* 6:195).

Although, the foregoing activation-specific complement system assays provide additional information regarding the status of specific complement system components in a sample, their complexity, lack of sensitivity and, in some cases, requirement of radioactive materials has prevented their widespread adoption and use for routine clinical diagnostic purposes. Thus, a need exists for improved methods for evaluating the in vivo status of the inflammatory response of a patient which overcomes the problems associated with prior art processes and reagents.

SUMMARY OF THE INVENTION

It has now been discovered that the foregoing problems associated with prior art processes and reagents can be overcome by improved methods wherein the presence or amount of in vivo inflammation of a patient is determined by comparing the extent of opsonin receptor expression in vido on phagocytes of a patient with the maximum opsonin receptor expression inducible on phagocytes of the patient in vitro after stimulation with a receptor expression priming agent. Preferably, the in vivo state of inflammation of a patient is determined by contacting a first portion of a phagocyte containing biological sample from the patient with an opsonified oxidative metabolism stimulating agent capable of eliciting metabolic activation and with a chemiluminigenic substrate, contacting a second portion of the biological sample from the patient with an opsonin receptor expression priming agent, an opsonified oxidative metabolism stimulating agent capable of eliciting metabolic activation and a chemiluminigenic substrate, and then comparing the chemiluminescence response of the first and second portions of the sample as a measure of the immune response potential or state of inflammation of the patient. In other aspects of the invention, phagocyte function is quantitatively evaluated by measuring the phagocyte oxygenation capacity of a maximally opsonin receptor primed and stimulated biological sample of a patient; determining the specific oxygenation capacity per phagocyte in the sample, and comparing the specific oxygenation capacity to a set of controls representing the normal distribution of specific oxygenation capacity established from testing a large population. The specific oxygenation capacity of phagocytes in a biological sample is determined by contacting the sample with an opsonin receptor expression priming agent, an opsonified oxidative metabolism stimulating agent and a chemiluminigenic substrate, measuring the chemiluminescence response of the sample, determining the chemiluminescence response per phagocyte of the sample and comparing the response per phagocyte with that of the normal range of values. In yet other aspects of the invention, kits and reagents are provided for use in the practice of preferred methods of the invention.

BRIEF DESCRIPTION OF THE DRAWINGS

FIG. 1 is a graphic representation illustrating the comparison of the extent of opsonin receptor expression in vivo with the maximal expression of opsonin receptors in vitro as a measure of the status of in vivo inflammation of a patient, in accordance with one aspect of the invention.

FIG. 3 is a graphic representation of chemiluminescence response in accordance with the invention showing the effect of in vitro aging of phagocytes over a six-hour period prior to measurement.

FIG. 4 is a graphic representation of chemiluminescence response showing the effect of in vitro aging of phagocytes over a 26-hour period prior to measurement.

FIG. 5 is a graphic representation of chemiluminescence response in accordance with the invention showing the effect of incubation of diluted whole blood samples in vitro in the presence (o) and absence (.) of 100 pmol of N-formylmethionyl leucyl phenylalanine (N-fMLP).

DETAILED DESCRIPTION OF THE INVENTION

Figure 2A:
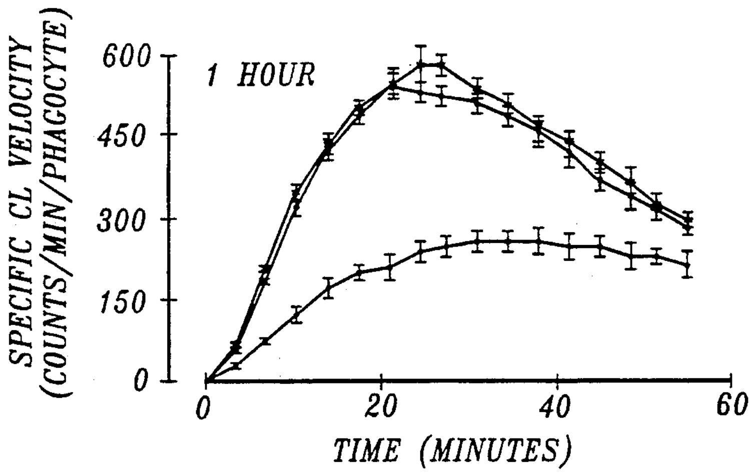
FIG. 2A is a graphic representation of the chemiluminescence responses from a diluted 1 μl equivalent whole blood sample of a healthy donor obtained in the practice of the invention, showing chemiluminescence velocity (counts/minute/phagocyte) versus time. As used in FIGS. 2-4, plot lines represented by (.), (o) and (*) represent the use of no receptor priming agent, a C5a receptor priming agent, or an N-fMLP receptor priming agent, respectively.

The present invention is broadly directed to methods for measuring the state of in vivo inflammation of a host. In accordance with one aspect of the present invention, the presence or amount of in vivo inflammation of a patient is determined by comparing the extent of opsonin receptor expression in vivo on peripheral phagocytes of a patient with the maximum opsonin receptor expression inducible on peripheral phagocytes in vitro after stimulation with a receptor expression priming agent. In the absence of a state of acute inflammation, opsonin receptors, e.g., C3b and N-fMLP receptors, are not fully expressed on peripheral phagocytes in vivo or as isolated in the presence of calcium chelating agents, e.g., citrate. As shown by Fearon and Collins, 1983, *J. Immunol.* 130:370, incubating isolated phagocytes at 37° C. for 30 min increases C3b receptor expression approximately eight-fold. Likewise, addition of purified $C5a_{desArg}$ or N-fMLP causes similar increases in C3b receptors. Warming the phagocytes also increases the expression of N-fMLP receptors but has no effect on $C5a_{desArg}$ receptor expression. Fearon et al., supra, conclude that $C5a_{desArg}$ receptors are fully expressed on peripheral phagocytes, but that N-fMLP and C3b receptor expression is largely latent. Since complement activation is essential for inflammation, C5a is a product of such complement activation, and C5a receptors are fully expressed on peripheral phagocytes but opsonin receptors, such as C3b receptors are not, the in vivo inflammatory state of a host may be quantitatively assessed as the index of opsonin receptor expression of the peripheral phagocytes of a biological sample of the host. Stated differently, the state of in vivo inflammation of the host is proportionally related to opsonin receptor expression of the circulating phagocyte, and can be measured as the ratio of receptor-dependent response of peripheral phagocytes in the in vivo condition relative to receptor-dependent response of maximally primed phagocytes, as schematically described in FIG. 1.

In an illustrative embodiment of this aspect of the invention, the in vivo state of inflammation of a patient, evaluated as the relative extent of opsonin receptor expression on peripheral phagocytes of a patient in their in vivo condition as compared with the extent of maximized opsonin receptor expression in vitro, is determined by a method comprising contacting a first portion of a phagocyte-containing biological sample from the patient with an opsonified oxidative metabolism stimulating agent capable of eliciting metabolic activation and with a chemiluminigenic substrate, contacting a second portion of the biological sample from the patient with an opsonin receptor expression priming agent, an opsonified oxidative metabolism stimulating agent capable of eliciting metabolic activation and a chemiluminigenic substrate, and then comparing the chemiluminescence response of the first and second portions of the sample as a measure of the immune response potential or state of inflammation of the patient.

In another aspect of the invention, a quantitative evaluation of total phagocyte function is made by measuring the phagocyte oxygenation capacity of a maximally opsonin receptor primed and stimulated biological sample of a patient, determining the specific oxygenation capacity per phagocyte in the sample, and comparing the specific oxygenation capacity to a set of controls representing the normal distribution established from testing a large population. In an illustrative embodiment of this aspect of the invention, the specific oxygenation capacities of biological samples of patients such as clinical blood samples, are determined by a method comprising contacting the samples with an opsonin receptor expression priming agent, an opsonified oxidative metabolism stimulating agent and a chemiluminigenic substrate, measuring the chemiluminescence response of the samples, determining the chemiluminescence response per phagocyte of the samples and comparing the response per phagocyte with that of a normal range of values generated from a population of lengthy controls.

Suitable opsonified-particulate oxidative metabolism stimulating agents ($S_{opsn}$) for use in the practice of the invention include opsonified materials which are recognized by the opsonin receptors of the phagocyte as "foreign" and therefore result in activation of "respiratory burst" redox metabolism in phagocytes in the sample. The agents are opsonified, such as by coating of the agent surface with protein materials, such as an immunoglobulin (IgG) or a complement-derived opsonin (e.g., C1, C3b or iC3b), which are specific for opsonin receptors, e.g., C3R or IgR, on the phagocytes. The opsonified oxidative metabolism stimulating agent may be opsonified attenuated bacteria, opsonified attenuated yeast or opsonified synthetic materials capable of fixing complement or eliciting specific antibody expression. In one representative embodiment, the opsonified oxidative metabolism stimulating agent is preferably opsonified zymosan, more preferably opsonified zymosan A, obtained by suspending a cell wall preparation of *Saccharomyces cerevisiae* in normal saline, heating the suspension to boiling, centrifuging the suspension and then suspending the pellet in pooled sera to opsonify the zymosan.

Suitable receptor expression priming agents include materials which interact with phagocytes to cause a net increase in the expression of functional surface opsonin receptors. Representative examples of suitable priming agents include C5a; $C5a_{desArg}$; N-formyl methionyl peptides characteristic of bacterial protein production, such as N-formyl methionyl leucyl phenylalanine (N-fMLP); leukotrienes, such as leukotriene $B_4$; platelet activating factor (PAF); and myeloid colony stimulating factors, such as granulocyte colony stimulating factor (G-CSF) and granulocyte-monocyte colony stimulating factor (G-CSF). Particularly presently preferred receptor expression priming agents include C5a and N-fMLP.

Circulating phagocytes, i.e., polymorphonuclear neutrophil leukocytes (PMNL) and monocytes (and probably eosinophils), fully express C5a receptors (C5aR) (approximately 50,000 per cell) without stimulation. However, receptors for the chemotactic N-formyl methionyl peptides (N-fMR) and for complement (C3b receptors, C3bR) [and probably also IgG, Fc receptors, FcR] opsonified material are not normally fully expressed on the circulating phagocytes (Fearon and Collins, 1983, *J. Immunol.* 130:370), as shown in Table 1.

TABLE 1

| | Number of Receptors Per Phagocyte | |
|---|---|---|
| Receptor | 4° C. | 20° C. |
| C5a | 53,400 | 43,000 |
| | 42,900 | 48,100 |
| N-fMLP | 14,700 | 41,699 |
| | 11,840 | 29,350 |
| C3b | 5,500 | 21,000 |
| | | 38,000 (at 37° C.) |

Conventional methodologies for measuring the presence of these receptors are techincally demanding, time consuming, and employ either radiosotopic techniques or require expensive flow cytometric equipment.

In essence, acute inflammation is the dynamic interaction between the humoral and phagocyte components of immunity in response to infection or injury. Circulating phagocytes provide the microbicidal effector arm of the acute inflammatory axis of immune defense. Phagocyte microbicidal activity is characterized by redox metabolism directed toward generating the oxygenating agents that under normal circumstances effect microbe killing. The resulting dioxygenation reactions are of relatively high energy and yield photon emission. Chemiluminescence, an energy product of phagocyte microbicidal function, is proportional to glucose metabolism via the hexose monophosphate phosphate shunt and $O_2$ consumption (Allen et al., 1972, *Biochem. Biophys. Res. Commun.* 47:679), as represented by the following equation.

$$CL=k[P_{Redox\ Metab}] \quad (1)$$

where CL is the chemiluminescence response expressed as either integral, intensity (velocity), change in intensity (acceleration) of the CL response, or the time required to reach some limiting condition (e.g., time to peak CL velocity or acceleration), k is the proportionality constant, and $[P_{Redox\ Metab}]$ is the extent of microbicidal metabolism, also referred to as the "respiratory burst".

Respiratory burst metabolism is directed to the generation of microbicidal oxygenating agents. The reaction of these agents with susceptible substrates can yield peroxides, endoperoxides, and dioxetane products that disintegrate to excited carbonyl functions that relax by photon emission, i.e., chemiluminescence. Thus, CL may be expressed as:

$$CL=k[Ox][Sub] \quad (2)$$

where CL and k have the meanings described above, Ox represents the oxygenating agents generated in microbicidal metabolism, and Sub represents the available substrates that can react with Ox to yield excited products and ultimately CL. The mechanisms whereby phagocytes generate oxygenating agents, and the nature and diversity of the oxygenation reactions yielding excited products is set forth in detail in Allen, 1986, *Meth. Enzymol.* 133:449.

The CL quantum yields, i.e., the photons per reaction, for native substrate oxygenations are relatively low and vary with the nature and molecular diversity of the substrates presented. Sensitivity as well as uniformity of response are achieved through the introduction of chemiluminigenic substrates (CLS), i.e., exogenous molecules that react with phagocyte generated oxygenating agents to yield excited products. Use of a suitable CLS, such as luminol or lucigenin, increases the sensitivity for detecting oxygenation activity by more than three orders of magnitude. The dioxygenation of luminol differs from the reductive dioxygenation of lucigenin, and these CLS can serve as probes for differentially assessing the nature of the oxygenation agents generated. (See Allen, 1982, in *Chemical and Biological Generation of Excited States*, Adam and Cilento eds., pp. 309-344, Academic Press, New York). Since the CLS becomes the substrate for obtaining excited-state reaction products, equation (2) above may alternatively be expressed as:

$$CL=k_1[Ox][CLS] \quad (3)$$

where CL, Ox, and CLS have the meanings described above and $k_1$ is the proportionality constant relative to the CLS employed.

Microbicidal metabolism and its energy product CL are not detected in unstimulated blood phagocytes. Such activation requires contact with opsonified particulate material, e.g., a C3b-labeled microbe, or artificial chemical stimulation, e.g., by contact with phorbol myristate acetate (PMA). The extent of redox metabolism, $P_{RedoxMetab}$, may be expressed as:

$$P_{Redox\ Metab}=c[P_{circ}][S_{opsn}] \quad (4)$$

where c is the proportionality constant for the condition described, $P_{circ}$ is the phagocyte in the unaltered circulating state, and $S_{opsn}$ is the immune opsonified microbe or equivalent.

C5a receptor capacity is maximally expressed in the unstimulated phagocyte; there are approximately 50,000 C5a receptors per phagocyte. However, N-fMLP, C3b and IgG receptors are latent, i.e., not maximally expressed, in circulating blood phagocytes (Fearon and Collins, 1983). Furthermore, the full expression of these receptors can be induced by in vitro exposure to a receptor expression priming agent, e.g., C5a. It is likely that maximal C5a receptor expression in unstimulated phagocytes reflects the crucial interactive link between C5a (and its still active cleavage product $C5a_{desArg}$) and the phagocyte effector arm of acute inflammation. It is also likely that the extent of a systemic inflammatory response is proportional to the extent of complement activation which is in turn proportional to the concentration of $C5a_{desArg}$ in the circulation. Phagocyte opsonin receptor expression is mostly latent in the unstimulated phagocyte, and functional expression is induced by exposure to $C5a_{desArg}$. As such, the in-circulation exposure of the phagocyte to $C5a_{desArg}$ results in proportional expression of opsonin receptors, as follows:

$$[Pcirc_{(Opsonin\ Recept)}]=b[C5a_{desArg}][P_{circ}] \quad (5)$$

where $[P_{circ(Opsonin\ Recept)}]$ represents the quantity of opsonin receptors expressed per circulating phagocyte, b is the proportionality constant and the other symbols have the meanings previously described. In effect, C5a and its cleavage product $C5a_{desArg}$, prime the phagocyte for contact recognition of immune opsonified material. The circulating lifetime of phagocytes is relatively short in the normal state, e.g., less than 12 hours for PMNL, and is further shortened by the inflammatory process. As such, opsonin receptor expression on the circulating phagocyte is dynamically and temporally linked to the in vivo state of inflammation.

As previously described, CL is an energy product of stimulated phagocyte redox metabolism. Activation of redox metabolism is normally through contact recognition of immune opsonified particles $[S_{opsn}]$ with opsonin receptors expressed on the phagocyte $[P_{circ}]$ as described in equation (4), and measurement of CL velocity, dCL/dt, provides a real time reflection of phagocyte metabolic activation kinetics:

$$dCL/dt=dP^*/dt=[P_{circOpsonin\ Recept}][S_{opsn}] \quad (6)$$

where dCL/dt is the CL velocity or intensity at any given time, dP*/dt is the velocity of oxidant generation by the activated phagocyte at that time, and the other variables are as previously described. Introduction of a suitable CLS insures high sensitivity and a degree of oxidant reactive specificity.

As will be demonstrated in Examples, the very small direct stimulatory effect of relatively high concentrations of a receptor expression priming agent, such as C5a, on phagocyte CL activity is negligible compared to the response induced by an opsonified oxidative metabolism stimulating agent, such as complement opsonified zymosan. However, the action of C5a on phagocyte opsonin receptor expression exerts a profound influence on the early kinetics of oxygenation activity, i.e., dP*/dt, and thus, on dCL/dt.

Thus, in accordance with one aspect of the invention, the presence and amount of in vivo inflammation can be measured as the extent of opsonin receptor expression on peripheral whole blood phagocytes. This value is obtained by comparing the opsonin receptor expression of in vivo circulating phagocytes to the maximum opsonin receptor expression induced by in vitro exposure to an optimum concentration of primer stimuli ($S_{maxprim}$) such as C5a, $C5a_{desArg}$, N-formyl peptides, etc., as described in FIG. 1.

When $[S_{opsn}]$ and [CLS] approximate the non-rate limiting condition, the initial rate of oxygenation activity, dP*/dt, and therefore, the initial rate of CL, dCL/dt, will reflect the opsonin receptor expression on the phagocyte. The CL response of phagocytes in a portion of untreated whole blood (CL, FIG. 1) can be simultaneously compared to the CL response of a second portion of the same sample in the presence of a receptor expression priming agent, $[S_{maxprim}]$, to yield full opsonin receptor expression as reflected in the initial rate of CL ($CL_{max}$, FIG. 1). As described in FIG. 1, the ratio of CL to $CL_{max}$ reflects the ratio of opsonin receptor expression in vivo to the maximum possible expression, and as such, the ratio provides an internally normalized expression of inflammatory condition in vivo.

In accordance with another aspect of the invention, the phagocyte specific oxygenation activity is determined and compared to a normal distribution of values constructed from healthy control donors. The integral CL response of $S_{opsn}$-treated blood correlates well with the phagocyte count of a specimen if integration is over a sufficiently long time interval (Allen and Pruitt, 1982, *Arch. Surg.* 117:133; Allen, 1982, *Adv. Exp. Med. Biol.* 141:411; *Proc. Int. Congr. Clin. Chem. 11th Edition*, 1981). However, correlation is decreased when attempts are made to use peak CL velocity or a relatively short time interval of integration. Four major reasons for this discrepancy between whole blood phagocyte count and phagocyte oxygenation activity are differences with respect to phagocyte: 1) opsonin receptors expression, 2) opsonin receptor content, 3) peroxidase content, and 4) oxidase content.

The combined use of $S_{prim}$ and $S_{opsn}$ eliminates the variable of opsonin receptor expression. The CL response from optimally primed, opsonin receptor-stimulated phagocytes reflects the functional specific oxygenation activity of phagocyte component in the whole blood specimen tested. Use of non-rate limiting concentrations of CLS, obviates the effect of substrate as a variable in the reaction. When luminol is the CLS, the CL response of primed and opsonin-receptor stimulated whole blood phagocytes reflects oxidase-driven haloperoxidase activity. The inhibitory effect of nanomole quantity of azide illustrates the major contribution of phagocyte haloperoxidase activities to the luminol-dependent CL response (Allen, 1986, *Meth, Enzymol.* 133:449). The phagocyte NAD(P)H:$0_2$ oxidoreductase generates $H_2O_2$, and is required for haloperoxidase function. However, the direct reaction of $H_2O_2$ with luminol is minimal at neutral pH.

Haloperoxidases are synthesized in the early promyelocyte phase of phagocyte development in the bone marrow. Whereas oxidase and receptor proteins are synthesized later in development. Inflammation and reactive consumption of phagocytes stimulates the rate of production and also influences the state of maturation of the various cytoplasmic components of the phagocyte. A large number of modulator glycoproteins such as Multipotent Colony Stimulating Factor (Multi-CSF) also known as Interleukin 3 (IL3), Granulocyte-Monocyte Colony Stimulating Factor (GM-CSF), and the specific factors, Granulocyte Colony Stimulating Factor (G-CSF), Monocyte Colony Stimulating Factor (M-CSF), and Eosinophil Colony Stimulating Factor (Eo-CSF), etc., are produced in inflammation in an attempt to maintain circulating phagocyte homeostasis. When supply exceeds consumption, a phagocyte leukocytosis or leukemoid response is observed. However, if phagocyte consumption outstrips production leukopenia results. Using appropriate CLS-medium, the CL activity of primed, opsonin receptor-stimulated whole blood reflects the phagocyte oxygenation capacity of the sample tested independent of the variable of opsonin receptor expression, and the limiting effect of CLS availability, and as such, provides a quantitative index of total phagocyte function.

When CL activity is expressed relative to phagocyte number, the specific oxygenation activity is obtained. In the presence of a non-limiting concentration of a CLS, such as luminol, the CL response of optimally primed opsonin receptor-stimulated phagocytes provides a means for evaluating the receptor content as well as the oxidase and peroxidase function of the blood phagocyte. As previously reported, phagocyte-specific oxygenation activity is typically low following severe injury (Allen and Pruitt, 1982); however, in this study the blood phagocytes were not primed and the CLS concentration (0.5 $\mu$M) was not adequate to insure against the CLS exerting a rate-limiting effect, as described herein.

There appears to be a good qualitative association between marrow stimulation associated with moderate injury or infection and an increased specific oxygenation activity when luminol is the CLS. Such an increase might reflect immune regulated optimization of phagocyte functional capacity in response to inflammation. Based on blood smear cytologic examination, increased specific oxygenation capacity appears to correlate best with cytoplasmic features of "toxic granulation", the prominence of PMNL primary granules in association with the inflammatory state. Primary or azurophilic granules are the first granules produced in the early promyelocyte. They are lysosomal in nature and contain haloperoxidase and acid optimum hydrolases. It is therefore likely that the observed increase in specific oxygenation activity with moderate inflammation reflects an increase in haloperoxidase content per phagocyte. However, it should be appreciated that optimum haloperoxidase function requires optimum receptor and oxidase function. For this reason, severe and/or prolonged stimulation of marrow production could result in diminished functionality.

Differential methods for evaluating the nonreceptor-dependent oxidase and oxidase-peroxidase functional capacities of phagocytes can be constructed by using chemical agents that bypass receptor-linked mechanisms for oxidase activation and selecting CLS probes that differentiate oxidase, e.g., lucigenin, from oxidase plus peroxidase activities, e.g., luminol. (See Allen, 1986, *Methods in Enzymology*, Vol. 133, pp. 449-493).

Suitable chemiluminigenic substrates (CLS) for use in the practice of the invention may be any substrate which is catalytically oxidized by singlet molecular oxygen ($^1O_2$), by peroxide, by hypohalite or by hypohalite and peroxide, produced in the course of phagocyte redox metabolism, to obtain an excited state oxidized reaction product that relaxes to a lower energy state with the emission of measurable light.

In one presently preferred, illustrative embodiment, the chemiluminigenic substrate may be a cyclic hydrazide that yields peroxide or endoperoxide intermediates under the reaction conditions described herein. Suitable cyclic hydrazides include compounds of the formula:

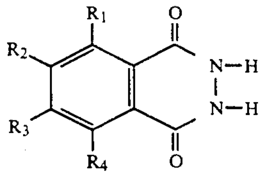
(7)

wherein $R_1$ is amino, amido, substituted amino or substituted amido, and $R_2$, $R_3$, $R_4$ are each independently selected from H, optionally substituted $C_1$–$C_6$ alkyl or alkenyl, hydroxyl, $C_1$–$C_6$ alkoxyl, carboxyl, amino, amido, substituted amino or substituted amido, or $R_1$ and $R_2$ taken together are an amino, amido, substituted amino or substituted amido derivative of a benzo group. Presently particularly preferred substrates of this embodiment of the invention are 5-amino-2,3-dihydro-1,4-phthalazinedione (luminol), 6-amino-2,3-dihydro-1,4-phthalzainedione (isoluminol) and 7-dimethylamino-naphthylene-1,2-dicarbonic acid hydrazide.

In general, the cyclic hydrazides undergo electrophilic dioxygenation in the presence of singlet molecular oxygen ($^1O_2$) to produce an unstable peroxide or endoperoxide intermediate, the intermediate rapidly rearranges to the corresponding electronically excited phthalate and the excited-state phthalate relaxes by the emission of light.

In another presently preferred, illustrative embodiment of the invention, the chemiluminigenic substrate may be any dioxetane precursor that reacts with singlet molecular oxygen or other oxygenating agents generated by the metabolically activated phagocyte to produce the corresponding unstable or stable 1,2-dioxetane compound. The production of unstable 1,2-dioxetanes is accompanied by rapid dioxetane breakdown yielding electronically excited carbonyl product which relaxes by the emission of light. Suitable 1,2-dioxetane precursors for use as chemiluminigenic substrates in the practice of the invention include alkenes lacking reactive allylic hydrogen atoms and enamines, as described in Kopecky, "Synthesis of 1,2-Dioxetanes," *Chemical and Biological Generation of Excited States*, Academic Press, pp. 85-144, 1982, which react with singlet molecular oxygen to produce the corresponding 1,2-dioxetane as follows:

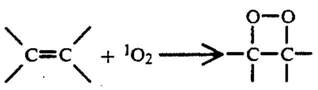
(8)

Representative examples of such dioxetane precursors are known in the art. See, for example, Wieringa et al., *Tetrahedron Lett.*, pp. 169-172, 1972; Bartlett et al., *J. Am. Chem. Soc.*, Vol. 96, pp. 627-629, 1974; Schaap, *Tetrahedron Lett.*, pp. 1757-1760 (1971); Schaap et al., *J. Am. Chem. Soc.*, Vol. 99, pp. 1270 et seq., 1977; Zaklika et al., *J. Am. Chem. Soc.*, Vol. 100, pp. 318-320 and pp. 4916-4918, 1978; and Zaklika et al., *Photochem. Photobiol.*, Vol. 30, pp. 35-44, 1979.

The physical characteristics of the light (or photon) emission resulting from the luminescent reaction described herein is primarily dependent upon the nature and properties of the chemiluminigenic substrate. When luminol is used as the chemiluminigenic substrate, the maximal spectral emission is in the region of 430–500 nm (blue-green light). The light emission produced may be detected by any photosensitive detector having adequate sensitivity in the part of the spectrum in which the luminescent substrate has its maximum spectral emission. For optimal measurement, the detector instrument should be temperature controlled and operable at 37° C.

The intensity of light emitted at an initial point in or over an initial interval of time is proportional to the rate of receptor-dependent phagocyte oxidative metabolism, and is therefore related to the extent of phagocyte opsonin receptor expression. The velocity (dhv/dt) or intensity (I) of the light emitted by the phagocyte increases from a base background level when the phagocytes, opsonified oxidative metabolism stimulating agent and chemiluminigenic substrate are mixed, to a peak velocity, and thereafter decreases to the base background level. Accordingly, the kinetics of the CL response during the period from initiation to peak velocity reflects the rate limiting influence of opsonin receptor expression on activation of phagocyte redox metabolism. In addition, other kinetic expressions of the light emitted by the system may be used to directly or indirectly determine the amount of phagocyte oxidative metabolic activity in a biological sample. For example, the total emitted light (i.e., the integral or sum of the number of photons emitted over a specified time interval), the peak emitted light velocity, the peak acceleration (i.e., $d^2h\nu/(dt)^2$ or d(Velocity)/dt) of light emission, or the highest value of integral, velocity or acceleration of luminescence measured within a predetermined time interval can be used as a determinative measure. Accordingly, the apparatus employed for measuring light emitted by the assay system may additionally comprise suitable mechanical or electronic apparatus as may be required for carrying out the measurement, derivation or integration of the data, data storage and analysis functions, as may be desired.

The biological sample to be analyzed may be a naturally occurring or artificially formed liquid containing the phagocytes of a patient. As used herein, the term "patient" includes both human and non-human animal subjects having phagocytes as an integral component of their immune system. In most cases, the liquid sample will be a biological fluid or a liquid resulting from the treatment or dilution of a biological fluid, such as whole blood, synovial, amniotic, cerebrospinal, peritoneal, pleural, pericardial fluids and fluids derived therefrom, such as serum, plasma and separated or artificially reconstructed phagocyte-containing biological fluids. It is a particular advantage of the invention that measurements can be made directly on small whole blood samples. Accordingly, in many cases, the biological sample will be diluted whole blood.

In yet another aspect of the invention, reagents are provided in kit form to facilitate ease of use, reproducibility of results and enhanced sensitivity of the methods for evaluation of the in vivo state of inflammation of a patient or the humoral-immune modulated specific activity of phagocytes described herein. Kits of the invention comprise one or more of the primary reagents used in the practice of the invention, i.e., an opsonin receptor expression priming agent, an opsonified oxidative metabolism stimulating agent and a chemiluminigenic substrate, as described above. These reagents may be provided in concentrated form for subsequent dilution and use, or preferably, are provided at optimal dilution for direct use in the performance of the methods of the invention.

In a presently particularly preferred embodiment, the opsonin receptor expression priming agent is provided in dry form, precoated on a solid surface adapted for use in a luminometer or other luminescence measuring device. For example, the opsonin receptor expression priming agent may be precoated in dry form on the inside surface of a light-transmissive tube which is suitable for forming a reaction container for receiving the sample to be analyzed and other kit reagents, and for direct insertion into a luminometer for chemiluminescence measurement. Light-transmissive containers of this type will preferably contain at least about 1 pmol of the opsonin receptor expression priming agent. When the priming agent is C5a, the container will preferably be coated with about 1 pmol to about 100 pmol of C5a, more preferably, about 15 pmol to about 25 pmol of C5a, and most preferably, about 10 pmol of C5a. When the priming agent is N-fMLP, the container will preferably be coated with about 25 pmol to about 500 pmol of N-fMLP, more preferably with about 50 to about 200 pmol of N-fMLP, and most preferably, about 100 pmol of N-fMLP. The precise amount of opsonin receptor expression priming agent to be employed in the kit will depend upon the concentration of phagocytes in the biological sample to be tested, and on other factors, but should be sufficient to obtain maximal expression of opsonin receptors on phagocytes in the sample. When the opsonin receptor expression priming agent is C5a, the use of too high a concentration of C5a may result in phagocyte response inhibition. When the opsonin receptor expression priming agent is N-fMLP, too high a level of N-fMLP may result in direct, opsonin receptor-independent oxidative activity. Accordingly, precise concentrations of reagents to be employed in the practice of the invention are preferably carefully designed to obtain optimum results.

While the opsonified oxidative metabolism stimulating agents and chemiluminigenic substrates of the invention are presently preferably provided in liquid form for direct use in the practice of the invention, as is hereafter further described in detail, it should be understood that these reagents may be provided in the kits of the invention in dry form, if desired. In addition, suitable ancillary materials, such as buffers, diluents, inert proteins, stabilizers, and the like, may be provided in the kits of the invention, as desired.

The foregoing may be better understood in connection with the following representative examples, which are presented for purposes of illustration and not by way of limitation.

EXAMPLES

Materials

Materials for use in the Examples were prepared as follows:

Preparation of Luminol Complete Medium (LCM)

Components for LCM and Blood Diluting Medium (BDM)

A. Preparation of sodium/potassium salt 10× concentrate (NaK-10XC):

1. NaCl, 54 grams
2. KCl, 2.6 grams
3. qs (quantum sufficit) to 1 liter with distilled $H_2O$.

B. Preparation of phosphate salt 100× concentrate ($PO_4$-100XC):
1. $KH_2PO_4$, 6 grams
2. $Na_2HPO_4.7H_2O$, 9 grams
3. qs to 1 liter with distilled $H_2O$.

C. Preparation of magnesium sulfate chloride 100× concentrate (Mg-100XC):
1. $MgSO_4.7H_2O$, 10 grams
2. $MgCl_2.6H_2O$, 10 grams
3. qs to 1 liter with distilled $H_2O$ D. Preparation of calcium chloride 100× concentrate (Ca-100XC):
1. $CaCl_2.2H_2O$, 18.5 grams
2. qs to 1 liter with distilled $H_2O$ E. Preparation of 20% (w/v) D-glucose:
1. D-glucose, 200 grams
2. qs to 1 liter with distilled $H_2O$ F. Preparation of 5% (w/v) gelatin, porcine (300 Bloom):
1. Gelatin, porcine (Sigma Chem. G2500), 50 grams
2. qs to 1 liter with boiling distilled $H_2O$
3. Heat in 90° C. bath until dissolved G. Preparation of 5% (w/v) albumin:
1. Albumin, human (Sigma Chem. A8763) globulin-free, 50 grams
2. Pass through a 0.45 micron filter
3. qs to 1 liter with distilled $H_2O$ H. Preparation of 0.5M luminol (5-amino-2,3-dihydro-1,4-phthalazinedione):
1. luminol, 4.43 grams
2. qs to 50 ml with dimethyl sulfoxide (DMSO), 99+% pure I. Preparation of 0.5M 2-[N-morpholino]ethanesulfonic (MES) acid:
1. MES acid, 97.5 grams
2. qs to 1 liter with distilled water J. Preparation of 0.5M Na 2-[N-morpholino]ethanesulfonate:
1. NaMES, 108.5 grams
2. qs to 1 liter with distilled $H_2O$ K. Pen-Strep Antibiotic: 10,000 units penicillin and 10 mg streptomycin per ml, (Sigma Chem. P0781).

One liter of LCM was prepared by mixing together the following proportions of the reagents listed above:
1. 0.5M MES, 0.73 ml
2. 0.5M NaMES, 9.27 ml
3. NaK-10XC, 144.13 ml
4. $PO_4$-100XC, 10.00 ml
5. 20% D-glucose, 5.00 ml
6. 5% gelatin, 20.00 ml
7. qs to 800 ml with distilled $H_2O$ and mix well.

To this solution, the following proportions of reagents, listed above, were added with mixing:
8. 0.5M luminol, 0.30 ml
9. Ca-100XC, 10.00 ml
10. Mg-100XC, 10.00 ml
11. Pen-Strep, 10.00 ml The pH of the LCM mixture was adjusted to a value in the range of 7.2 to 7.3 with NaOH, and distilled water was added qs to one liter (final volume). The osmolality was measured and the luminol concentration determined by absorbance spectroscopy using an extinction coefficient of 7.6 $mM^{-1}cm^{-1}$ at 350 nm. The final concentration of luminol in the LCM was 0.15 mM; this concentration is approximately three times the Michaelis constant (Allen, 1986, *Meth. Enzymol.* 133:449). The osmotic strength of LCM was set within the range 285 to 295 mOsm/kg.

The LCM was passed through a 0.45 micron filter to insure sterility and stored at refrigerator temperature (approximately 4° C.) until used.

Preparation of Blood Diluting Medium (BDM)

Whole blood diluting medium (BDM) was prepared by mixing together the following proportions of components described above.
1. 0.5M MES, 0.60 ml
2. 0.5M NaMES, 9.40 ml
3. NaK-10XC, 160.00 ml
4. $PO_4$-100XC, 10.00 ml
5. 20% D-glucose, 5.00 ml
6. 5% gelatin, 10.00 ml
7. Pen-Strep, 10.00 ml
8. qs to 900 ml with distilled $H_2O$ and mix well.

The pH of the BDM mixture was adjusted to within the range 7.2 to 7.3 with NaOH and distilled water was added to the solution qs to a final volume of one liter. The osmolality of the BDM was set within the range of 285 to 295 mOsm/kg. The BDM was passed through a 0.45 micron filter to insure sterility. The BDM was dispensed to sterile tubes and kept refrigerated (approximately 4° C.) until used for whole blood dilution.

Preparation of Complement Opsonified Zymosan (COpZ)

Preparation of Globulin-Free Plasma (GFP)

One liter of pooled fresh-frozen human plasma (testing negative for human immunodeficiency virus (HIV) antibody, HIV p24 core antigen, hepatitis B surface antigen, and syphilis serology (VDRL)) was placed in 6.4 cm diameter dialysis tubing (Spectra/Por 1), molecular cutoff 6,000 to 8,000, and dialyzed against four equivalent volumes of 28.5% saturated ammonium sulfate (SAS) for 2 hours at 22° C. The SAS solution was exchanged with fresh four volumes of 28.5% SAS and the plasma was dialyzed overnight at 4° C.

The plasma was centrifuged at 500 relative centrifugal force (RCF) for 40 to 60 minutes and the clear supernatant was separated from precipitated protein. The clear supernatant portion of the plasma was placed in new dialysis tubing and dialyzed for 3 hours at 22° C. against 10 equivalent volumes of Hank's balanced salt solution without $Ca^{++}$ or $Mg^{++}$. The balanced salt solution was changed to a fresh 10 volumes of HBSS without $Ca^{++}$ and $Mg^{++}$ and the supernatant was dialyzed overnight at 4° C. to obtain the dialyzed globulin-free plasma (GFP). The remaining levels of immunoglobulin and the complement components C3, C4, Factor B, and total hemolytic complement were measured and the GFP was found to be greater than 95% free of the immunoglobulins. Approximately 75% of the antigenic complement and greater than 80% of the functional complement activity was retained in the GFP.

Preparation of Zymosan A

Five grams of zymosan A from Saccharomyces cerevisiae (Sigma Chem. Z4250) was suspended in one liter of 0.9% NaCl (normal saline), and the suspension was placed in a 90° C. water bath for 30 minutes with constant stirring. The suspension was allowed to cool to room temperature, and centrifuged at 200 RCF for 10 min. The supernatant was discarded and the pellet (zymosan) was resuspended in fresh saline to the original volume. The zymosan was stored refrigerated (4° C.)

until used. The particle (cell wall remnants) count of this suspension was approximately 4,000,000 per microliter.

Opsonification of Zymosan

One volume of the zymosan (Z) suspension described above was added to two volumes of GFP. The GFP-Z suspension was activated by addition of 0.185 gram $CaCl_2.2H_2O$ and 0.1 gram $MgSO_4$. $7H_2O$ per liter of GFP. The suspension was gently mixed for 10 minutes at room temperature 22° C., and then centrifuged at 200 RCF for 10 minutes. The supernatant was removed (and saved for extraction of $C5a_{desArg}$). The pellet was resuspended in 2 equivalent volumes of ice cold normal saline, mixed for 10 minutes, and centrifuged as above. The supernatant was discarded and this saline wash-centrifugation cycle was repeated twice, to obtain washed opsonified zymosan.

The opsonified zymosan (COpZ) was resuspended to original volume with normal saline. The resulting suspension had approximately 2,500,000 to 3,000,000 COpZ particles per microliter. With continuous mixing the COpZ suspension was aliquoted to containers and quick frozen. The COpZ was maintained frozen, below −40° C., until being thawed for use. Once thawed, the COpZ was kept refrigerated (not refrozen).

Preparation of Primer Stimuli Test Tubes

Preparation of N-formyl-1-methionyl-1-leucyl-1-phenylalanine (N-fMLP) coated test tubes A 250 mM stock solution of N-fMLP (Sigma Chem. F3506) was prepared by dissolving 250 mg N-fMLP in 2.28 ml of DMSO (99+% pure). This stock was diluted with methanol to a 10 mM substock solution. This substock was further diluted 1 to 10,000 with methanol to yield a solution containing 100 picomoles (pmol) per 100 microliters.

One hundred microliters (0.1 ml) per tube of this solution was dispensed to plastic (polystyrene) test tubes. The methanol was allowed to evaporate, thus coating the tube with 100 pmol N-fMLP. This quantity of N-fMLP is optimal for priming the phagocytes in one microliter of blood without chemically activating respiratory burst metabolism. The N-fMLP tubes were stored dry at room temperature till used.

Preparation of C5a-coated test tubes

A 10 μm stock solution of C5a (recombinant human, Sigma Chem. C5788) was prepared by dissolving 0.1 mg (11.6 nanomoles) C5a in 1.16 ml DMSO. This 10 μM substock was diluted 1 to 100 with methanol, and 0.1 ml (100 μl) per tube of the diluted solution dispensed to plastic (polystyrene) test tubes. The solvent methanol was evaporated, thus coating each tube with 10 pmols of C5a. This is the optimal quantity of C5a to prime the phagocytes present in one microliter equivalent of blood. The tubes were stored dry at room temperature until used.

Preparation of PMA-coated tubes

A 10 mM stock was solution of phorbol 12-myristate 13-acetate (PMA; also called 12-0-tetradecanoylphorbol 13-acetate) was prepared by dissolving 10 mg of PMA in 1.62 ml of DMSO. This 10 mM stock PMA was diluted by adding 1.62 ml of the stock solution to 322 ml of methanol with stirring, to obtain a 50 μM PMA solution. 0.1 ml (100 μl) of the diluted PMA solution per tube was dispensed to plastic (polystyrene) test tubes. The solvent methanol was evaporated, thus coating the tube with 5 nanomoles (nmol) of PMA. This is the optimum quantity of PMA to direct elicit a luminol-dependent CL response from phagocytes in a one microliter equivalent sample of blood. The tubes were stored dry at room temperature until used.

PROTOCOL FOR IN VIVO PHAGOCYTE RECEPTOR EXPRESSION ANALYSIS

Venous, capillary, or arterial blood collected by venipuncture, indwelling lines, or capillary puncture (finger stick) can serve as a suitable blood sample for use in the practice of the invention. Likewise, any other phagocyte-containing body fluid, e.g., spinal fluid, synovial fluid, etc., may be similarly tested. Unless the blood or other specimen tested is immediately diluted by adding the sample to BDM, e.g., in the ratio of 1 to 100 (i.e., 100 μl of sample to 9.9 ml of BDM) and analyzed shortly thereafter, the sample should be immediately anticoagulated, e.g., with either sodium or potassium ethylenediamine tetraacetate (EDTA) or citrate. The sodium or potassium EDTA vacuum collection tubes routinely employed in hematology for complete blood counts are easily obtained and can be employed in this regard. In addition to serving as anticoagulants, these $Ca^{++}$ and $Mg^{++}$ chelating agents also inhibit complement activation in vitro and as such stabilize the collected specimen by protecting against complement activation and in vitro generation of C5a and $C5a_{desArg}$, thus insuring that the observed alterations in C3b expression are a reflection of the in vivo condition. In the experiments described below, the blood was maintained at room temperature, i.e., 22° C., during the premeasurement, post collection period.

In the experiments described, temperature-controlled Berthold 950 luminometers were used for chemiluminescence measurement; this type of luminometer uses 12×44 mm test tubes, and as such, polystyrene test tubes with these dimensions were employed for testing. The reagents COpZ and LCM, prepared as described above, were placed on a heating block and allowed to equilibrate at 38° to 40° C. The BDM was allowed to equilibrate to room temperature before being employed for sample dilution.

Except as otherwise described below, for each sample test, eight hundred microliters (800 μl) of the heated LCM and one hundred microliters (100 μl) of heated COpZ were added to each uncoated, C5a-coated, and N-fMLP-coated test tube, and the tubes were immediately loaded into a preheated luminometer set at 38° C. The blood specimen was then added to BDM as described above and one hundred microliters (100 μl) of the diluted specimen was automatically injected into each tube at the time of initiation of measurement. The luminescence intensity (CL velocity) was measured for 0.1 sec and the value obtained is expressed as counts/-minute, counts/minute, or kilocounts/minute/-phagocyte. The samples were continuously cycled and counted in the instrument for the period of testing indicated.

The data shown in FIG. 2 were obtained from a diluted whole blood sample of a healthy individual. Approximately 4 to 5 ml of blood was collected by venipuncture into a sterile vacuum (lavender top hematology) tube containing fifty microliters (50 μl) 15% $K_3EDTA$ (7.5 mg). The blood was placed on a tilt Table to insure gentle mixing. The test tubes containing warmed reagents were loaded into the luminometer. Uncoated, C5a-coated, and N-fMLP-coated tubes without COpZ were included as $S_{prim}$-positive, $S_{opsn}$-negative controls. Fifty microliters (50 μl) of the mixed EDTA-treated whole blood were added to 4.95 ml of BDM and the sample was analyzed within 30 minutes of dilution. One ml of the remaining whole blood specimen was used for complete blood count (CBC), and the remainder of the undiluted whole blood was kept at room temperature (22° C.) for future testing.

After gentle mixing to insure homogenous cell suspension, the BDM-diluted blood specimen was used to prime the injector pump and luminescence measurements were initiated by injection of one hundred microliter (100 μl) of the BDM-blood suspension per tube, i.e., each tube received a one microliter (1 μl) equivalent of whole blood. As indicated in FIGS. 2A, 2B and 2C, 17 measurements were taken over a period of approximately 55 minutes. Measurement was initiated approximately one hour post venipuncture, as indicated by the "1 Hour" notation at the top of FIGS. 2A, 2B and 2C. The data are plotted as the specific luminescence velocity per phagocyte versus the time in minutes. These values were obtained by dividing the measured CL velocity, i.e., counts pr minute, by the number of phagocytes in the blood specimen tested, i.e., the total leukocyte count per microliter minus the total lymphocyte count per microliter. The values of the total leukocyte and differential count were obtained by routine clinical hematology laboratory methodology. For this sample, the total leukocyte count was 7,300 per microliter (μl) with a differential count of 3,600 segmented PMNL, 50 band PMNL, 375 monocytes, 225 eosinophils and 3,250 lymphocytes per μl. As such, the phagocyte count, i.e., the total leukocyte count minus the total lymphocyte count, is estimated as 4,250/μl.

Figure 2B:
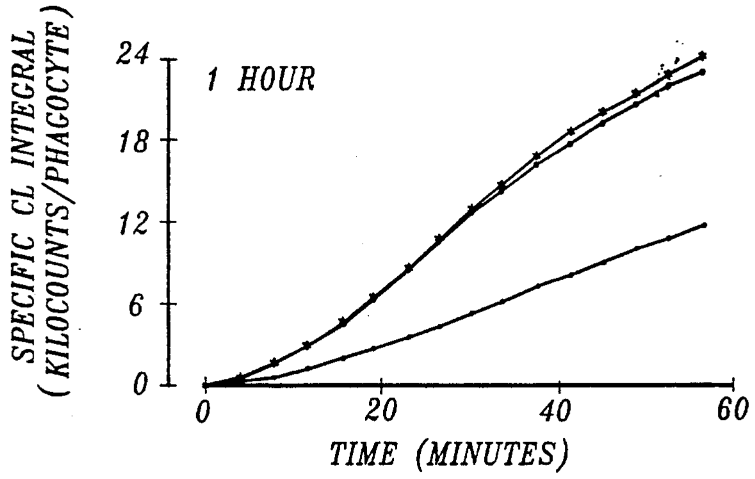
FIG. 2B is a plot of the integral (i.e., accumulated counts) of measured photons per phagocyte versus time.
Figure 2C:
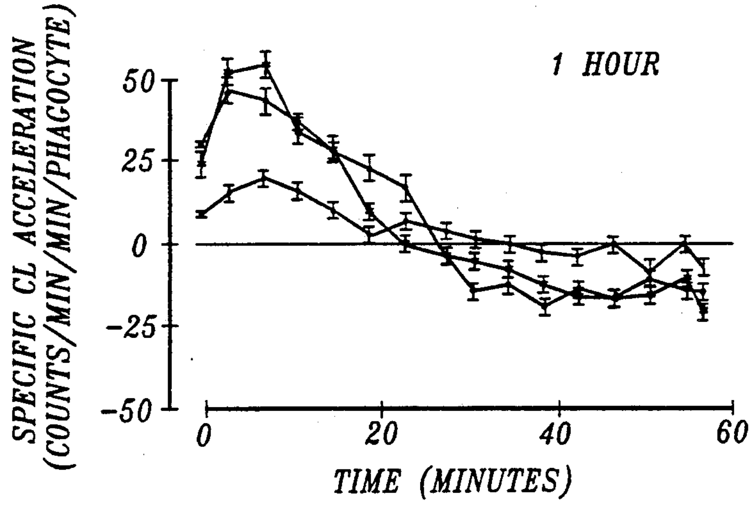
FIG. 2C is a plot of chemiluminescence acceleration versus time, shown as counts/minute/minute/phagocyte or $d^2$ counts/$(dt)^2$, the first derivative of chemiluminescence velocity.

In FIGS. 2A, 2B and 2C, the curve without symbols (.) represents the data obtained using uncoated tubes, i.e., without incorporated primer stimulus; the curve marked with (o) symbols is the response obtained using tubes coated with 10 pmol C5a; the curve marked with (*) depicts the response obtained using tubes coated with 100 pmol N-fMLP. All tubes contained 100 μl COpZ as the opsonin receptor stimulus. All tests were run in triplicate, and in the figures, the standard deviations are indicated by the error bars. Tubes containing primer stimulus only, i.e., without COpZ, yielded peak CL velocities approximately twice those obtained in the absence of primer stimuli. However, these velocities were two orders of magnitude lower than those obtained with COpZ, and as such, they are not shown in the figures.

Luminometry is the measurement of CL velocity, i.e., the intensity of photons (photons/unit time) striking the photocathode is proportional to the intensity of the electric current (electrons/unit time) through the collector anode. The current is processed to yield the counts/unit time. Techniques, such as absorption spectroscopy, are also based on light measurements, but the signal measured is secondary to the disappearance of substrate or accumulation of product with change in time, i.e., an integral or summation value with respect to the interval time period of measurement. In CL measurements, the photon is the product measured, and as such, the measurement of luminescence intensity at any given point in time reflects the photon emission at that time. FIG. 2A depicts the change in CL velocity with change in time. FIG. 2B plots the integral or accumulated counts versus time; i.e., this integral depiction treats the photon as an accumulated product thus approximating the type of data curve routinely obtained by other product accumulation methods. The values for the data in FIG. 2B were calculated from the data of FIG. 2A by trapezoidal approximation. The direct measurement of CL velocity offers advantages with respect to real time dynamic analysis and is analogous to derivative absorption spectroscopic techniques which convert product accumulation data to velocity (d(product)/dt).

The change in CL velocity with change in time reflects the acceleration of CL emission to a maximum or peak velocity value. In FIG. 2A, these peak values with standard deviations (SD) are 252±21, 525±32, and 581±41 counts/minute/phagocyte where $S_{prime}$ is none, C5a, and N-fMLP respectively and COpZ is the $S_{opsn}$. The times from initiation to peak velocities are 38±3, 28±3, and 29±2 minutes, respectively. The peak velocity response to $S_{prim}$ (C5a) in the absence of $S_{opsn}$ (COpZ) was 5±, the peak phagocyte response in the absence of $S_{prim}$ and $S_{opsn}$ was 3±0, and the combined machine-reagent background activity in the absence of phagocytes was 2±1. After reaching peak velocity, the phagocyte enters the slower deceleration phase of activity. Note that the greater the initial acceleration, the greater the rate of deceleration.

The dynamics of the primer-opsonin receptor interaction can be best appreciated by plotting the data as the CL acceleration, i.e., the counts/minute/minute (the derivative of the velocity; dcounts/minute/dt or $d^2$counts/$(dt)^2$) versus time as depicted in FIG. 2C. The values for change in velocity are positive when the CL response is in the acceleration phase, goes through zero at peak velocity, and are negative in the deceleration phase. Comparison of FIGS. 2A, 2B and 2C provides a perspective of the dynamics of stimulated phagocyte oxygenation activity as analyzed by its product CL. The abscissa is common to all of the graphics.

Although analysis of receptor dynamics can be based on integral, velocity, or acceleration descriptions of the luminescence response, the use of acceleration provides certain advantages. Since CL acceleration is the change in CL velocity, measurement is focused on phagocyte activation dynamics, an acceleration process. For example, a constant photon emitting standard (based on luminescence resulting from the radioactive decay of chemically quenched tritium, $^3H$; see Seliger, H. H., 1978, *Meth. Enzymol.* 57:560) used for luminometer calibration had a peak CL velocity of approximately 100 kilocounts/minute, but because this velocity is essentially constant, no acceleration is observed. As shown in FIG. 2C, the early portion of the acceleration phase best illustrates the differences in activation kinetics induced by the $S_{prim's}$ C5a and N-fMLP. By 5.2 minutes, i.e., the time midpoint between the 3.5 and 6.9 minutes post initiation velocity measurements, the CL acceleration values with SDs were 13.1±1.3, 39.0±1.7, and 35.4±2.2. counts/min/min/phagocyte where $S_{prim}$ was none, C5a, and N-fMLP, respectively. The $S_{prim}$ tubes contain optimum C5a or N-fMLP for priming the phagocytes in the blood specimen tested. The $S_{opsn}$ COpZ is adjusted to provide a non-limiting quantity of C3b opsonified particles. As such, the rate of activation CL is proportional to the available opsonin receptors of the phagocyte tested.

With regard to the experimental data as represented in FIG. 2, incorporation of C5a or N-fMLP as $S_{prim}$ resulted in a three-fold increase in acceleration with respect to the activity of phagocytes in the absence of added primer. The activation dynamics of untreated phagocytes reflect the state of in vivo priming. If there is active in vivo inflammation, the inflammation-associated primers such as C5a, $C5a_{desArg}$, cytokines, and products of lipid metabolism, serve to prime the expression of phagocyte opsonin receptors in vivo. As such, the difference in CL activation dynamic will be diminished in proportion to the extent of in vivo inflammation, i.e., in vivo inflammation results in a loss of opsonin receptor reserve. If the initial 5 min CL acceleration values are compared, the ratio of unprimed to C5a-primed CL is 0.34±0.05 and the ratio of unprimed to N-fMLP-primed CL is 0.37±0.06. As such, the opsonin reserve based on C5a and N-fMLP priming is 66% and 63%, respectively.

Figure 3A:
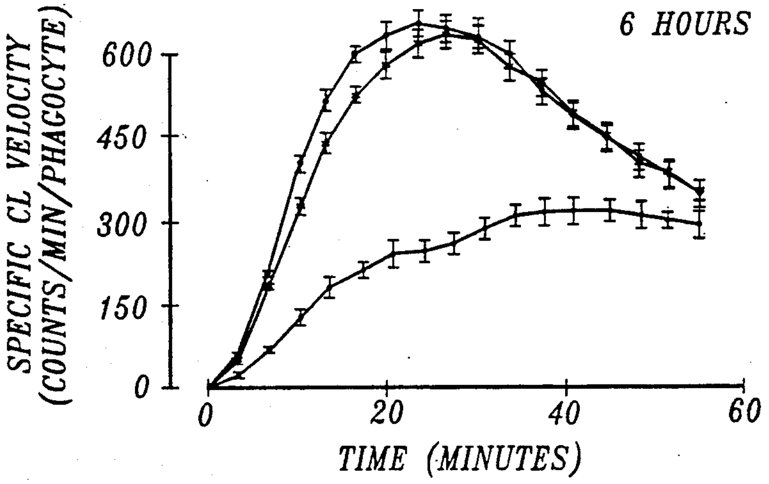
FIG. 3A is a plot of the chemiluminescence velocity versus time obtained from a diluted whole blood sample starting at a time six hours post-venipuncture (PVP).
Figure 3B:
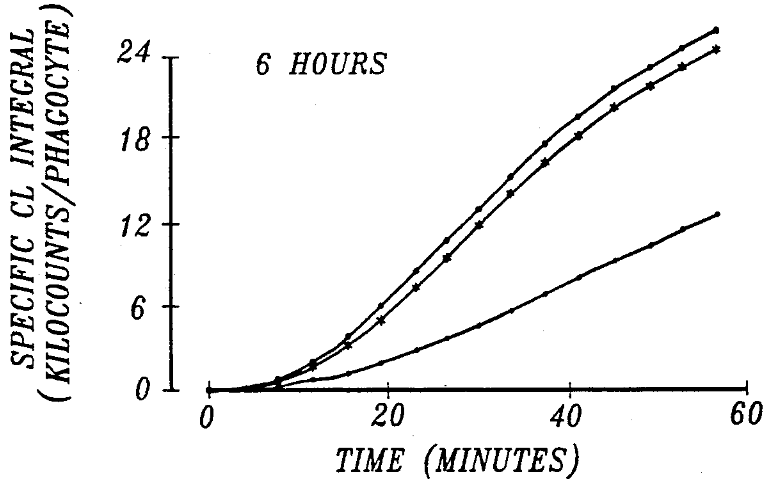
FIGS. 3B and 3C are plots of the integral of measured chemiluminescence and acceleration of the same data, respectively.
Figure 3C:
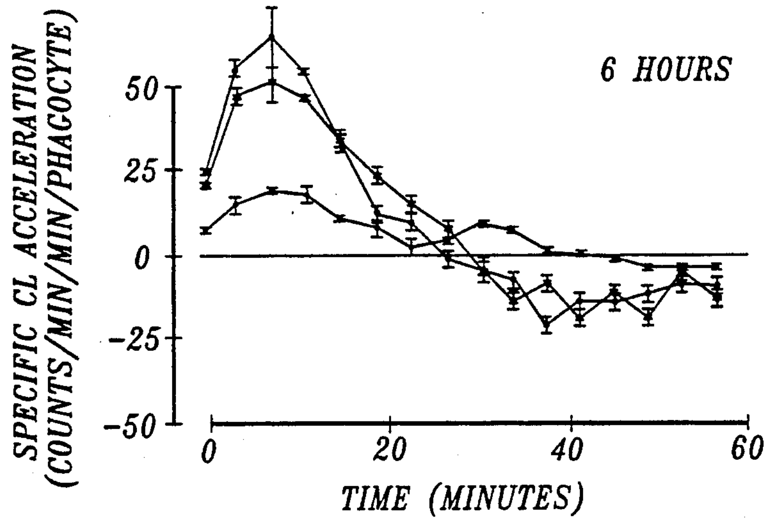
Figure 4A:
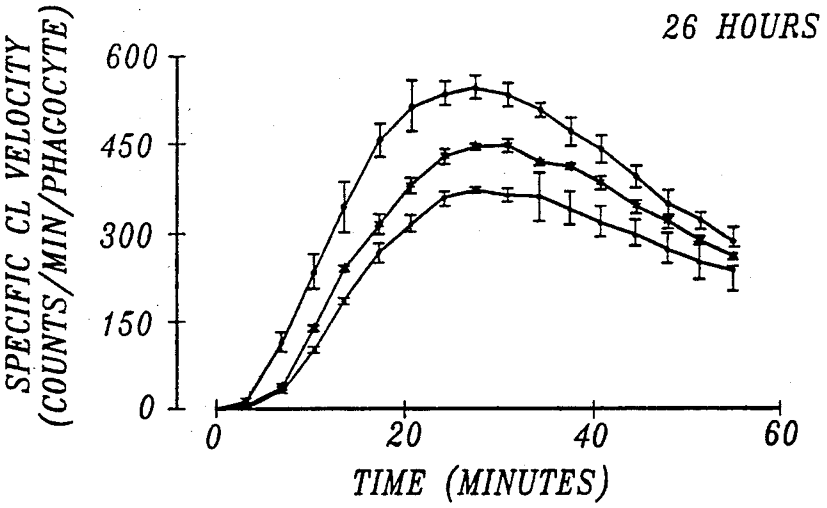
FIG. 4A is a plot of the chemiluminescence velocity versus time starting at a time 26 hours PVP.
Figure 4B:
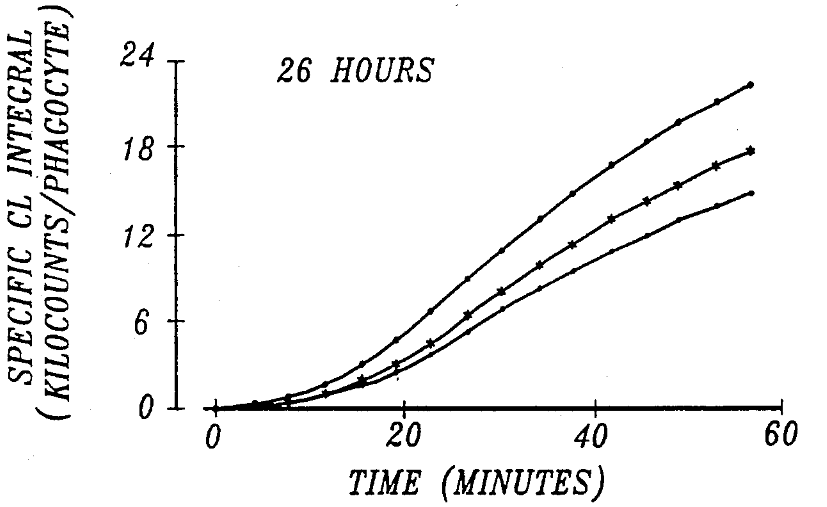
FIGS. 4B and 4C are plots of the integral of measured chemiluminescence and acceleration of the same data, respectively.
Figure 4C:
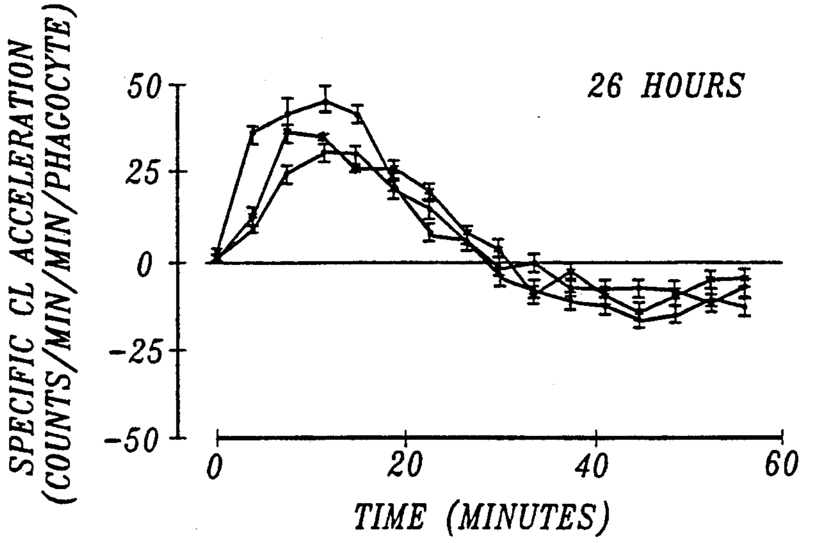
Figure 5A:
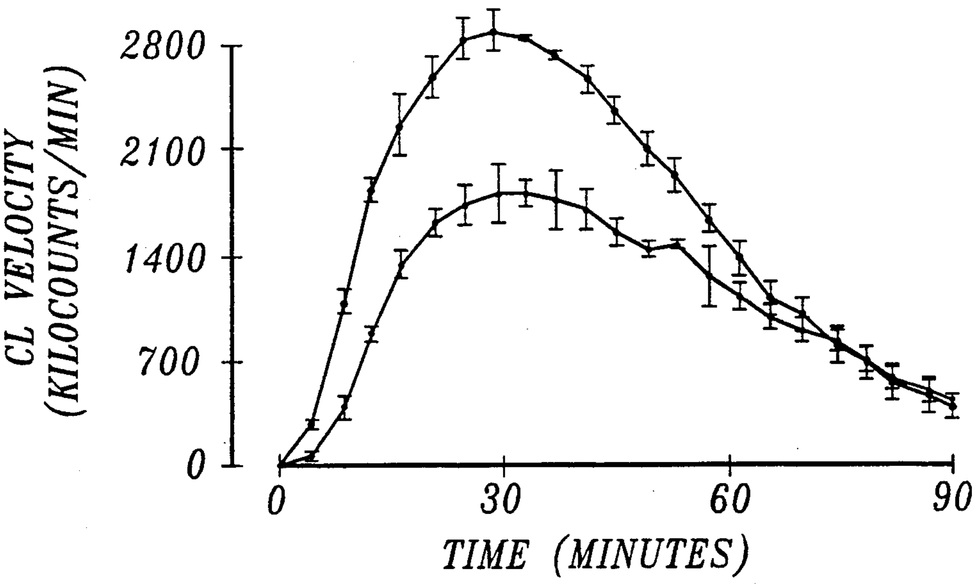
FIG. 5A is a plot of the chemiluminescence velocity, CL (in kilocounts/minute), versus time when the sample is contacted with both N-fMLP and opsonified zymosan at time zero.
Figure 5B:
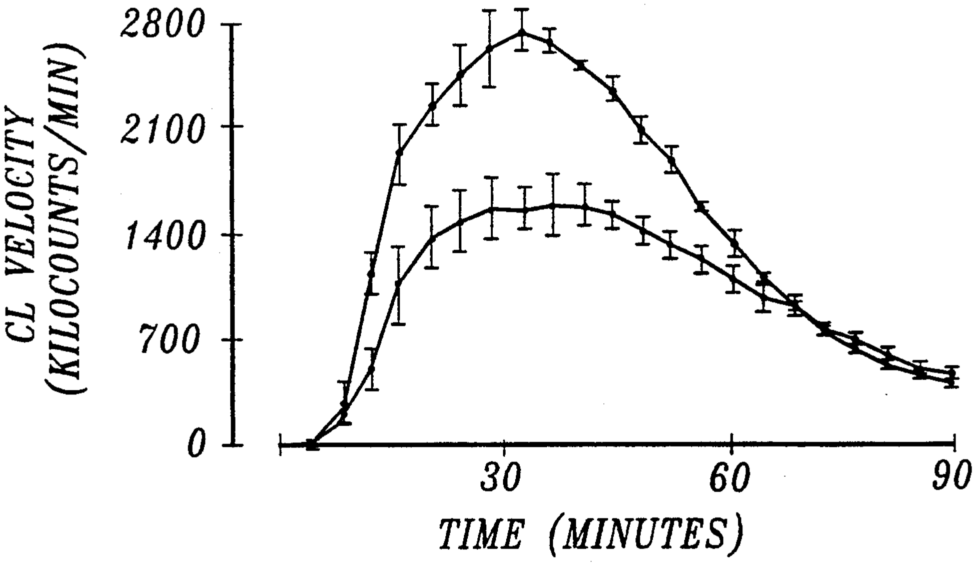
FIGS. 5B, 5C and 5D are corresponding plots where the sample is incubated for 4 minutes, 20 minutes, and 30 minutes respectively, with the N-fMLP prior to contact with opsonified zymosan.
Figure 5C:
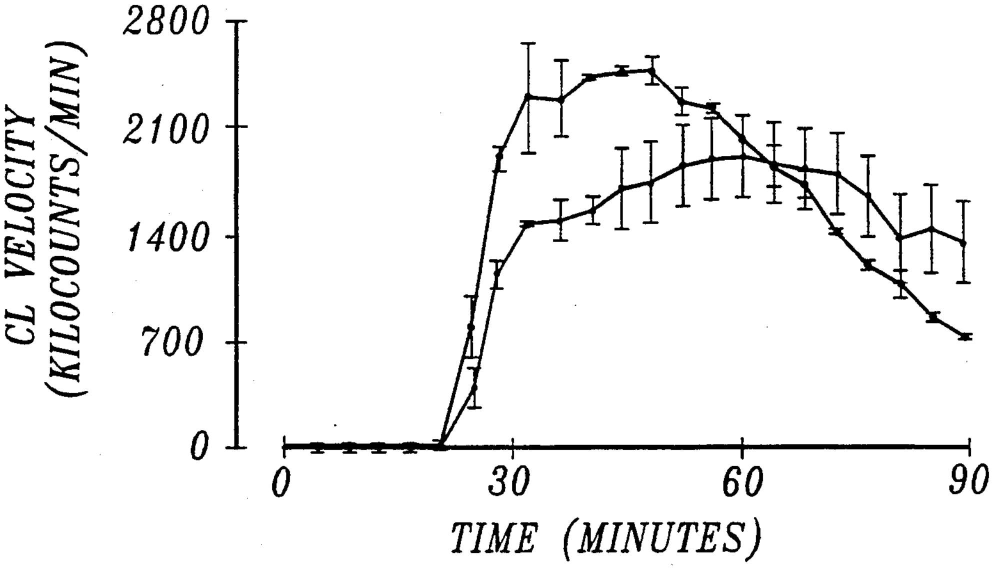
Figure 5D:
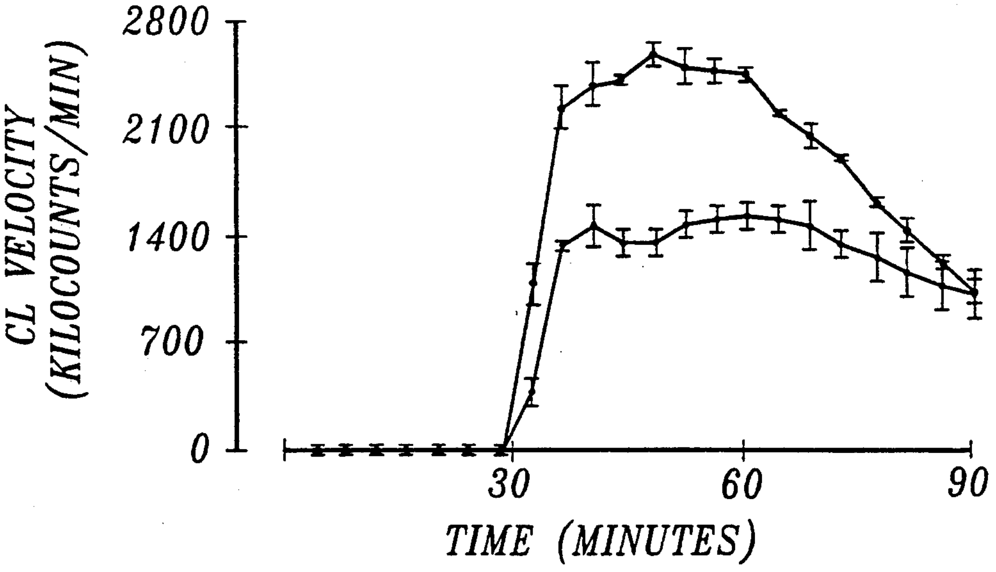

To establish the stability of blood phagocytes to functional changes induced by in vitro aging, testing of the same blood specimen was repeated at 6, 26 and 33 hours postvenipuncture. During this period the whole blood specimen was maintained at 22° C. The blood specimen was diluted in BDM just prior to testing. The results of the six-hour study are presented in FIGS. 3A, 3B and 3C and the results of the 26-hour study are presented in FIGS. 4A, 4B and 4C. With the exception of blood in vitro age, the conditions were as described above.

The CL responses of the six hours postvenipuncture phagocytes (FIG. 3) are comparable to those obtained at one hour (FIG. 2) with respect to both magnitude, activation kinetics, and opsonin receptor reserve. The changes induced at 26 hours (FIG. 4) are more obvious. At 26 hours, there is a decrease in response to N-fMLP priming, e.g., the peak CL velocity drops to 453±16 counts/minute/phagocyte and the CL acceleration is delayed; the 5.2 min acceleration drops to 10.2±0.8 counts/min/min/phagocyte, and there is an increased responsiveness in the absence of primer, e.g., the peak CL velocity is increased to 376±11 and is obtained earlier, i.e., at 36±4 minutes. The C5a-primed, COpZ-stimulated response is very well maintained, as is the opsonin receptor reserve based on the unprimed to C5a-primed initial (5 min) CL acceleration ratio, 0.30±0.10 (i.e., 70% reserve). Due to the large decrease in initial (5 min) CL acceleration, there is a large decrease in opsonin receptor reserve based on the unprimed:N-fMLP-primed initial acceleration values, i.e., 0.79±0.23 (or 21% receptor reserve).

The initial acceleration values for CL (COpZ), $CL_{max}$ (C5a-COpZ), the CL:$CL_{max}$ ratio, as well as the values obtained using the opsonin receptor independent chemical stimulus phorbol myristate acetate (precoated 5 nmol PMA tubes) are presented in the following Table 2 for the 33 hours post venipuncture (PVP) interval:

TABLE 2

Effect of Postvenipuncture Age on Immune and Chemically Elicited CL

| Time, post venipuncture | CL COpZ | CLmax C5a:COpZ | CL/CLmax | CL (chemical) PMA |
|---|---|---|---|---|
| 1 hour | 13.1 ± 1.3 | 39.0 ± 1.7 | 0.34 ± 0.05 | 31.3 ± 2.7 |
| 6 hours | 12.8 ± 2.0 | 40.4 ± 4.3 | 0.33 ± 0.09 | 29.9 ± 2.1 |
| 26 hours | 7.9 ± 1.7 | 28.4 ± 3.9 | 0.30 ± 0.10 | 6.6 ± 0.6 |
| 33 hours | 6.6 ± 1.9 | 13.2 ± 1.3 | 0.52 ± 0.20 | 6.1 ± 0.4 |

Values are in CL Acceleration: Counts/min/min/phagocyte (between 3.4 and 6.9 min post initiation)

The data of Table 2 illustrate the relative stability of the phagocyte response to submaximal and maximal immune stimulation in comparison to chemical stimulation of metabolism. The maximally primed, opsonin receptor stimulated phagocyte response is the most robust as well as the best retained over time.

The composite data of FIGS. 5A, 5B, 5C and 5D depict the effects of various time intervals of exposure of blood phagocytes to uncoated (.) and 100 pmol N-fMLP coated (o) tubes prior to addition of COpZ. The data are presented as CL velocity in kilocounts/minute versus time in minutes over a 90 minute interval of testing. The donor was a healthy female and the total white blood cell (WBC) count minus the lymphocyte count was 6,600/μl. The conditions were as previously described except that COpZ was added at various time periods, e.g., approximately 0, 4, 20, and 30 minutes as shown in FIGS. 5A, 5B, 5C and 5D, respectively, following the addition of the BDM-diluted whole blood at time zero.

These data illustrate that exposure to a priming dose of N-fMLP does not directly elicit a significant CL response, but this priming dose does produce a significant change in the temporal kinetic response to COpZ. Similar results are obtained with C5a. It is also evident from these data that prolonged primer exposure time produces more rapid acceleration but lower peak velocity.

CLINICAL SAMPLING

The preliminary data presented in the following Table 3 are a compilation of results obtained by testing in accordance with the invention on hospital blood specimens drawn for clinical hematologic evaluation. The results shown in Table 3 are less than optimum in that CL testing was on the day following venipuncture, and as such the significance of intermediate values for the opsonin receptor ratio is questionable. However, very high values, such as seen for the patient with bacterial pneumonia, suggest a very active ongoing inflammatory process.

TABLE 3

Comparison of COpZ, C5a - COpZ, and PMA Elicited Responses from Blood Phagocytes of Clinical Patients with Bacterial or Viral Infections

| Patient: Age (yrs.) | Sex | Disease Condition | WBC - Lymphocytes (per microliter) | PVP Age (hours) | CL* COpZ | CLmax* C5a:COpZ | CL/CLmax | CL* (Chemical) PMA |
|---|---|---|---|---|---|---|---|---|
| Bacterial infection, Mild to Moderate: | | | | | | | | |
| 10 | M | Cellulitis, leg | 8,800–1,940 | 24 | 21.3 ± 2.8 | 28.9 ± 5.0 | 0.78 ± 0.23 | 11.9 ± 1.9 |
| 14 | F | Appendicitis | 19,100–1,340 | 24 | 30.6 ± 6.0 | 45.8 ± 1.5 | 0.68 ± 0.16 | 13.4 ± 2.7 |
| 5.4 | F | Pneumonia | 16,400–1,800 | 32 | 63.6 ± 8.0 | 68.7 ± 8.3 | 0.96 ± 0.24 | 19.1 ± 1.4 |
| Bacterial Infection, Severe: | | | | | | | | |
| 0.2 | F | Meningitis | 16,200–5,180 | 13 | 8.7 ± 0.6 | 11..4 ± 0.5 | 0.77 ± 0.09 | 8.1 ± 1.7 |
| 0.6 | M | Meningitis | 29,100–4,660 | 28 | 3.9 ± 0.5 | 4.5 ± 0.2 | 0.83 ± 0.11 | 3.8 ± 0.7 |

TABLE 3-continued

Comparison of COpZ, C5a - COpZ, and PMA Elicited Responses from Blood Phagocytes of Clinical Patients with Bacterial or Viral Infections

| Patient: | | | WBC - Lymphocytes | PVP Age | CL* | CLmax* | | CL* (Chemical) |
|---|---|---|---|---|---|---|---|---|
| Age (yrs.) | Sex | Disease Condition | (per microliter) | (hours) | COpZ | C5a:COpZ | CL/CLmax | PMA |
| Viral Infection, Mild to Moderate: | | | | | | | | |
| 0.8 | M | Pneumonia | 12,400–3,840 | 32 | 35.1 ± 7.2 | 60.7 ± 12.3 | 0.63 ± 0.25 | 54.3 ± 4.6 |
| 0.3 | M | Pneumonia | 14,300–6,720 | 29 | 15.8 ± 1.0 | 19.5 ± 1.5 | 0.82 ± 0.11 | 3.3 ± 0.6 |
| Viral Infection, Severe: | | | | | | | | |
| 0.2 | M | Meningitis | 7,400–4,660 | 13 | 11.7 ± 1.9 | 14.4 ± 0.5 | 0.82 ± 0.16 | 13.5 ± 1.4 |

*CL activities are expressed as counts/minute/minute/phagocyte (measured between 3.3 and 6.6 min post initiation).

These data confirm that the immune functional capacity of the phagocytes in a biological sample best correlates with the CL response of optimally primed, opsonin receptor activated phagocytes. In general, mild to moderate bacterial infections are associated with increased phagocyte capacity. The highest activities were measured from phagocytes in the two moderate bacteria infected patients. These patients also presented evidence of marrow stress; e.g., the phagocyte count of the appendicitis patient contained 1,910 band PMNL/μl and the phagocyte count of the bacterial pneumonia had 2,130 band PMNL and 330 metamyelocytes/μl.

The two cases of severe bacterial infections, i.e., meningitis, demonstrated depressed phagocyte function. The band PMNL counts of these patients were 490/μl and 1,160/μl for the first (upper) and last (lower) patients, respectively.

On the other hand, phagocyte capacity is generally decreased in patients with mild to moderate viral infection. The band PMNL counts for the two viral pneumonias were 620/μl and 570/μl for first (upper) and second (lower), respectively. The band PMNL count for the viral meningitis patient was 70 band PMNL/μl. The relatively high specific activity of the phagocytes from the first viral pneumonia patient is associated with a well maintained reserve, i.e., a low CL:$CL_{max}$ ratio, despite the postvenipuncture age of this specimen.

Various modifications and applications of the methods of the invention will be apparent from the foregoing to those skilled in the art. Any such modifications and applications are intended to be within the scope of the appended claims except insofar as precluded by the prior art.

What is claimed is:

1. A method of evaluating the in vivo state of inflammation of a patient, comprising:

a) determining the extent of opsonin receptor expression on phagocytes in a first portion of a phagocyte-containing biological sample of a patient, b) contacting a second portion of the biological sample with receptor expression priming agent to obtain maximal expression of opsonin receptors on phagocytes in the second portion of the biological sample;

c) determining the extend of opsonin receptor expression on phagocytes in the second portion of the sample; and then d) comparing the extent of opsonin receptor expression on the phagocytes of the first and second portions of the sample as a measure of the in vivo state of inflammation of the patient.

2. The method of claim 1 wherein the patient is a human or animal patient and the biological sample comprises a diluted or undiluted biological fluid selected from the group consisting of whole blood, synovial fluid, amniotic fluid, cerebrospinal fluid, peritoneal fluid, pleural fluid, pericardial fluid, and fluids derived therefrom.

3. The method of claim 2 wherein the biological sample is diluted or undiluted whole blood.

4. The method of claim 1 wherein the extent of opsonin receptor expression is determined by contacting the first and second portions of the sample with an opsonified oxidative metabolism stimulating agent and a chemiluminigenic substrate, and then measuring the chemiluminescence response of phagocytes in the first and second portions of the sample as an indication of the extent of receptor expression.

5. The method of claim 4 wherein first and second portions of the sample are contacted with non-rate limiting quantities of the opsonified oxidative metabolism stimulating agent and the chemiluminigenic substrate.

6. The method of claim 5 wherein the second portion of the sample is contacted with a non-rate limiting quantity of the receptor expression priming agent.

7. The method of claim 4 wherein the opsonified oxidative metabolism stimulating agent is coated with one or more of the members of the group consisting of immunoglobulin and complement-derived opsonins.

8. The method of claim 4 wherein the opsonified oxidative metabolism stimulating agent is selected from the group consisting of opsonified attenuated bacteria, opsonified attenuated yeast and opsonified synthetic materials capable of fixing complement or eliciting specific antibody expression.

9. The method of claim 8 wherein the opsonified oxidative metabolism stimulating agent is opsonified zymosan.

10. The method of claim 1 wherein the receptor expression priming agent is selected from the group consisting of C5a, $C5a_{desArg}$, N-formyl-methionyl peptides, leukotrienes, platelet activating factor, and myeloid colony stimulating factors.

11. The method of claim 10 wherein the receptor expression priming agent is C5a or $C5a_{desArg}$.

12. The method of claim 10 wherein the receptor expression priming agent is an N-formyl-methionyl peptide.

13. The method of claim 12 wherein the receptor expression priming agent is N-fMLP.

14. The method of claim 2 wherein the chemiluminigenic substrate is a cyclic hydrazide.

15. The method of claim 14 wherein the cyclic hydrazide is a 2,3-dihydro-1,4-phthalazinedione.

16. The method of claim 15 wherein the cyclic hydrazide is selected from a group consisting of luminol, isoluminol and 7-dimethylamino-naphthalene-1,2-dicarbonic acid hydrazide.

17. The method of claim 2 wherein the chemiluminigenic substrate is a dioxetane precursor capable of reacting with singlet-multiplicity molecular oxygen to produce a dioxetane or a dioxetanone.

18. A method of evaluating the systemic immune reserve of a patient, comprising:

a) contacting a first portion of a phagocyte-containing biological sample from the patient with an opsonified oxidative metabolism stimulating agent and a chemiluminigenic substrate;

b) contacting a second portion of the sample with a receptor expression priming agent, an opsonified oxidative metabolism stimulating agent and a chemiluminigenic substrate;

c) measuring the chemiluminescence responses of the first and second portions of the sample; and d) comparing the chemiluminescence responses of the first and second portions of the sample as an indication of the systemic immune reserve of the patient.

19. The method of claim 18 wherein the patient is a human or animal patient and the biological sample comprises a diluted or undiluted biological fluid selected from the group consisting of whole blood, synovial fluid, amniotic fluid, cerebrospinal fluid, peritoneal fluid, pleural fluid, pericardial fluid, and fluids derived therefrom.

20. The method of claim 19 wherein the biological sample is diluted or undiluted whole blood.

21. The method of claim 18 wherein the opsonified oxidative metabolism stimulating agent is coated with one or more of the members of the group consisting of immunoglobulin and complement-derived opsonins.

22. The method of claim 18 wherein the opsonified oxidative metabolism stimulating agent is selected from the group consisting of opsonified attenuated bacteria, opsonified attenuated yeast and opsonified synthetic materials capable of fixing complement or eliciting specific antibody expression.

23. The method of claim 22 wherein the opsonified oxidative metabolism stimulating agent is opsonified zymosan.

24. The method of claim 18 wherein the receptor expression priming agent is selected from the group consisting of C5a, $C5a_{desArg}$, N-formyl-methionyl peptides, leukotrienes, platelet activating factor, and myeloid colony stimulating factors.

25. The method of claim 24 wherein the receptor expression priming agent is C5a or $C5a_{desArg}$.

26. The method of claim 24 wherein the receptor expression priming agent is an N-formyl-methionyl peptide.

27. The method of claim 26 wherein the receptor expression priming agent is N-fMLP.

28. The method of claim 18 wherein the chemiluminigenic substrate is a cyclic hydrazide.

29. The method of claim 28 wherein the cyclic hydrazide is a 2,3-dihydro-1,4phthalazinedione.

30. The method of claim 29 wherein the cyclic hydrazide is selected from a group consisting of luminol, isoluminol and 7-dimethylamino-naphthalene-1,2-dicarbonic acid hydrazide.

31. The method of claim 18 wherein the chemiluminigenic substrate is a dioxetane precursor capable of reacting with singlet-multiplicity molecular oxygen to produce a dioxetane or a dioxetanone.

32. A method of evaluating the humoral-immune modulated specific activity of phagocytes in a phagocyte-containing biological sample of a patient, comprising:

a) contacting the sample with a receptor expression priming agent, an opsonified oxidative metabolism stimulating agent and a chemiluminigenic substrate, b) measuring the chemiluminescence response of the sample, c) determining the approximate number of phagocytes in the sample;

d) determining the specific chemiluminescence response per phagocyte in the sample as a measure of phagocyte specific activity; and d) comparing the phagocyte specific activity with those of a range of controls.

33. The method of claim 32 wherein the patient is a human or animal patient and the biological sample comprises a diluted or undiluted biological fluid selected from the group consisting of whole blood, synovial fluid, amniotic fluid, cerebrospinal fluid, peritoneal fluid, pleural fluid, pericardial fluid, and fluids derived therefrom.

34. The method of claim 33 wherein the biological sample is diluted or undiluted whole blood.

35. The method of claim 32 wherein the opsonified oxidative metabolism stimulating agent is coated with one or more of the members of the group consisting of immunoglobulin and complement-derived opsonins.

36. The method of claim 32 wherein the opsonified oxidative metabolism stimulating agent is selected from the group consisting of opsonified attenuated bacteria, opsonified attenuated yeast and opsonified synthetic materials capable of fixing complement or eliciting specific antibody expression.

37. The method of claim 36 wherein the opsonified oxidative metabolism stimulating agent is opsonified zymosan.

38. The method of claim 32 wherein the receptor expression priming agent is selected from the group consisting of C5a, $C5a_{desArg}$, N-formyl-methionyl peptides, leukotrienes, platelet activating factor, and myeloid colony stimulating factors.

39. The method of claim 38 wherein the receptor expression priming agent is C5a or $C5a_{desArg}$.

40. The method of claim 38 wherein the receptor expression priming agent is an N-formyl-methionyl peptide.

41. The method of claim 39 wherein the receptor expression priming agent is N-fMLP.

42. The method of claim 32 wherein the chemiluminigenic substrate is a cyclic hydrazide.

43. The method of claim 42 wherein the cyclic hydrazide is a 2,3-dihydro-1,4-phthalazinedione.

44. The method of claim 43 wherein the cyclic hydrazide is selected from a group consisting of luminol and 7-dimethylamino-naphthalene-1,2-dicarbonic acid hydrazide.

45. The method of claim 32 wherein the chemiluminigenic substrate is a dioxetane precursor capable of reacting with singlet-multiplicity molecular oxygen to produce a dioxetane or a dioxetanone.

46. A kit for use in the evaluation of the in vivo state of inflammation of a patient or the humoral-immune modulated specific activity of phagocytes comprising:

a) an opsonin receptor expression priming agent in an amount sufficient to obtain maximal expression of opsonin receptors on said phagocytes but not so high as to result in direct, opsonin receptor-independent oxidative activity;

b) an opsonified oxidative metabolism stimulating agent; and c) a chemiluminigenic substrate.

47. The method of claim 46 wherein the opsonin receptor expression priming agent is selected from the group consisting of C5a, $C5a_{desArg}$, N-formyl-methionyl peptides, leukotrienes, platelet activating factor, and myeloid colony stimulating factors.

48. The kit of claim 47 wherein the receptor expression priming agent is C5a or $C5a_{desArg}$.

49. The kit of claim 47 wherein the receptor expression priming agent is an N-formyl-methionyl peptide.

50. The kit of claim 49 wherein the receptor expression priming agent is N-fMLP.

51. The kit of claim 46 wherein the opsonin receptor expression priming agent is coated on at least a portion of a light-transmissive container.

52. The kit of claim 46 wherein the opsonified oxidative metabolism stimulating agent is coated with one or more of the members of the group consisting of immunoglobulin and complement-derived opsonins.

53. The kit of claim 46 wherein the opsonified oxidative metabolism stimulating agent is selected from the group consisting of opsonified attenuated bacteria, opsonified attenuated yeast and opsonified synthetic materials capable of fixing complement or eliciting specific antibody expression.

54. The kit of claim 53 wherein the opsonified oxidative metabolism stimulating agent is opsonified zymosan.

55. The kit of claim 46 wherein the chemiluminigenic substrate is a cyclic hydrazide.

56. The kit of claim 55 wherein the cyclic hydrazide is a 2,3-dihydro-1,4-phthalazinedione.

57. The kit of claim 56 wherein the cyclic hydrazide is selected from a group consisting of luminol, isoluminol and 7-dimethylamino-naphthalene-1,2-dicarbonic acid hydrazide.

58. The kit of claim 46 wherein the chemiluminigenic substrate is a dioxetane precursor capable of reacting with singlet-multiplicity molecular oxygen to produce a dioxetane or a dioxetanone.

59. The kit of claim 51 having at least about 1 pmol of the opsonin receptor expression priming agent coated on the surface of said container.

60. The kit of claim 51 wherein the opsonin receptor expression priming agent is selected from the group consisting of C5a, $C5a_{desArg}$, N-formyl-methionyl peptides, leukotrienes, platelet activating factor, and myeloid colony stimulating factors.

* * * * *

UNITED STATES PATENT AND TRADEMARK OFFICE

CERTIFICATE OF CORRECTION

PATENT NO. : 5,108,899

DATED : April 28, 1992

INVENTOR(S) : Robert C. Allen

It is certified that error appears in the above-identified patent and that said Letters Patent is hereby corrected as shown below:

TITLE PAGE

| | | |
|---|---|---|
| [56] Other Publications | 8th Ref. | "Electric" should read --Electronic-- |
| [56] Other Publications | 11th Ref. | "Serun" should read --Serum-- |
| [56] Other Publications | 11th Ref. | "Chemiluninescent" should read --Chemiluminescent-- |
| [56] Other Publications | 15th Ref. | "Disease" should read --Diseases-- |
| [56] Other Publications | 18th Ref. | "Acadamic" should read --Academic-- |
| [56] Other Publications | 32nd Ref. | "Enzyne" should read --Enzyme-- |
| [56] Other Publications | 33rd Ref. | "McCara" should read --McCapra-- |
| [56] Other Publications | 33rd Ref. | "Immunos-say" should read --Immunoassay-- |
| [57] Abstract | 11 | "a opsonified" should read --an opsonified-- |
| [57] Abstract | 12 | "elicting" should read --eliciting-- |
| [57] Abstract | 15 & 16 | "opson-field" should read --opsonified-- |
| [57] Abstract | 28 | after "oxygenation" insert --capacity-- |

UNITED STATES PATENT AND TRADEMARK OFFICE

CERTIFICATE OF CORRECTION

PATENT NO. : 5,108,899

DATED : April 28, 1992

INVENTOR(S) : Robert C. Allen

It is certified that error appears in the above-identified patent and that said Letters Patent is hereby corrected as shown below:

| COLUMN | LINE | |
|---|---|---|
| 7 | 22 | "(G-CSF)" should read --(GM-CSF)-- |
| 7 | 45 | "techincally" should read --technically-- |
| 7 | 46 | "radiosotopic" should read --radioisotopic-- |
| 13 | 13 | "(dhv/dt)" should read --(dhυ/dt)-- |
| 19 | 26 | "pr" should read --per-- |
| 23 (Claim 1, Line 11) | 57 | "extend" should read --extent-- |
| 25 (Claim 29, Line 2) | 56 | "1,4phthalazinedione" should read --1,4-phthalazinedione-- |

Signed and Sealed this

Twelfth Day of October, 1993

Attest:

BRUCE LEHMAN

*Attesting Officer* *Commissioner of Patents and Trademarks*